United States Patent

Anno et al.

[11] Patent Number: 5,098,811
[45] Date of Patent: Mar. 24, 1992

[54] TONER FOR DEVELOPING ELECTROSTATIC LATENT IMAGE COMPRISING SPECIFIED IMIDAZOLES

[75] Inventors: Masahiro Anno; Hideaki Ueda, both of Osaka, Japan

[73] Assignee: Minolta Camera Kabushiki Kaisha, Osaka, Japan

[21] Appl. No.: 410,891

[22] Filed: Sep. 22, 1989

[30] Foreign Application Priority Data

| Sep. 22, 1988 [JP] Japan | 63-239428 |
| Sep. 22, 1988 [JP] Japan | 63-239429 |
| Sep. 22, 1988 [JP] Japan | 63-239430 |
| Sep. 22, 1988 [JP] Japan | 63-239431 |
| Sep. 22, 1988 [JP] Japan | 63-239432 |
| Aug. 11, 1989 [JP] Japan | 1-209089 |
| Aug. 11, 1989 [JP] Japan | 1-209090 |
| Aug. 11, 1989 [JP] Japan | 1-209091 |

[51] Int. Cl.$^5$ ............................................. G03G 9/00
[52] U.S. Cl. ........................................ 430/110; 430/109
[58] Field of Search ................................ 430/110, 109

[56] References Cited

U.S. PATENT DOCUMENTS

| 3,933,664 | 1/1976 | Nagashimi et al. | 430/106 |
| 4,258,116 | 3/1981 | Takasu et al. | 430/110 X |
| 4,761,358 | 8/1988 | Hosoi | 430/109 |
| 4,983,485 | 1/1991 | Nagaoka et al. | |

FOREIGN PATENT DOCUMENTS

| 59-187350 | 10/1984 | Japan . |
| 61-217055 | 9/1986 | Japan . |
| 62-287262 | 12/1987 | Japan . |

OTHER PUBLICATIONS

Complexes of 1,2 Dimethylimidazole with Divalent Cobalt, Ni, Cu, and Zinc, by D. M. L. Goodgame et al. J. Chem. Soc (A), 1971, pp. 1923–1927.

*Primary Examiner*—Marion E. McCamish
*Assistant Examiner*—Stephen Crossan
*Attorney, Agent, or Firm*—Burns, Doane, Swecker & Mathis

[57] ABSTRACT

This invention relates to a positively chargeable toner for developing electrostatic latent images comprising;
a resin,
a colorant, and
a charge controlling agent
wherein the charge controlling agent is a specified imidazole compound, and/or a homopolymer of a nitrogen-containing vinyl monomer or a copolymer thereof with styrene, and the resin may be a polyester resin or suspension polymerized polymer, which is unsuitable for positive chargeability in nature.

28 Claims, 1 Drawing Sheet

Synthesis Example 5 finer than 150 meshes or more : 0.7wt%
between 150~32 meshes : 92.3wt%
rougher than 16 meshes : 0wt%

$\overline{D_v}$ = 0.38mm
$\overline{D_l}$ = 0.29mm
$\overline{D_v}/\overline{D_l}$ = 1.31

Particle size (mesh)

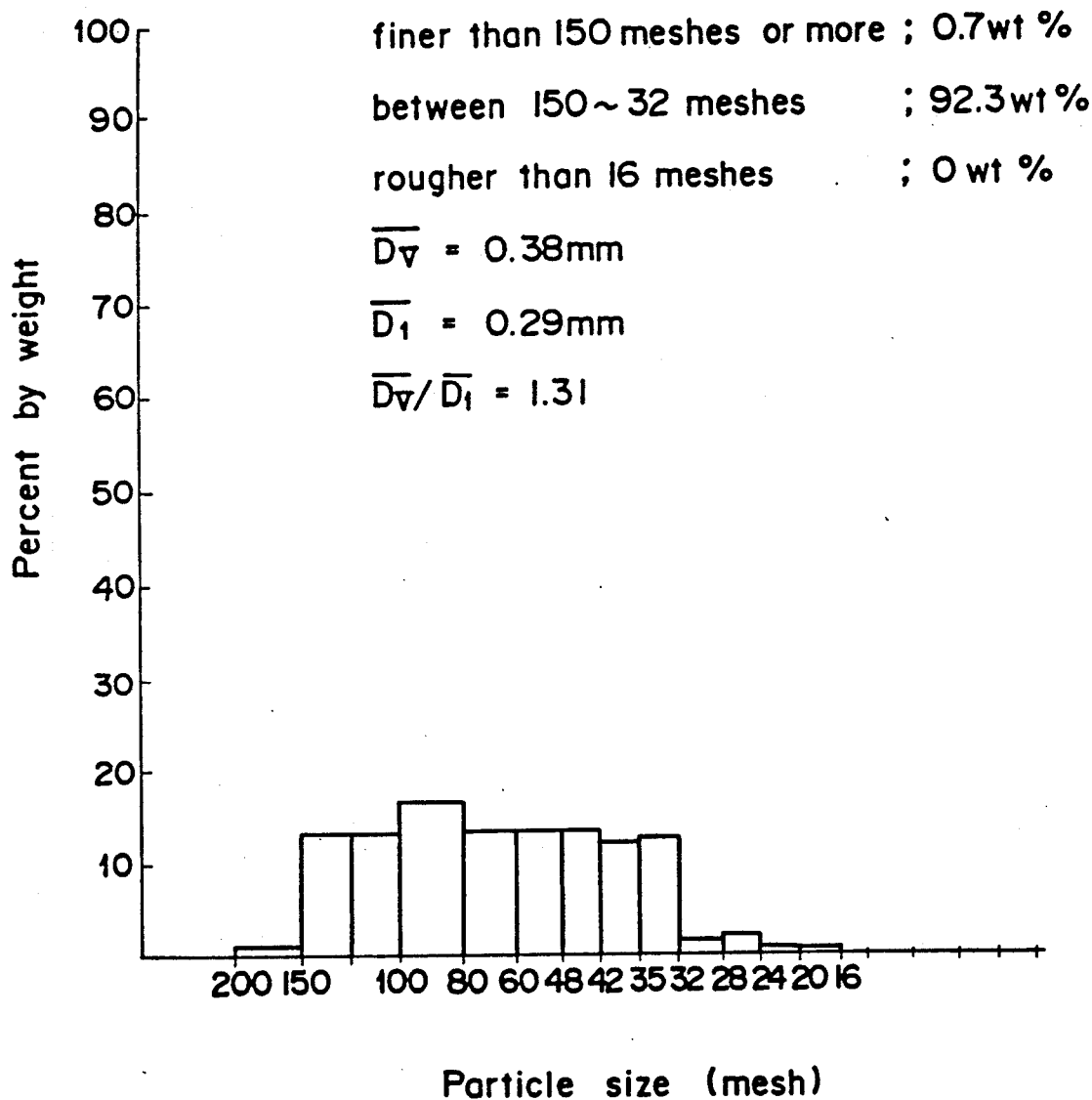

TONER FOR DEVELOPING ELECTROSTATIC LATENT IMAGE COMPRISING SPECIFIED IMIDAZOLES

BACKGROUND OF THE INVENTION

This invention relates to a toner for developing electrostatic latent images in electrophotography, electrostatic recording, electrostatic printing or the like, in more particularly, excellent in positive chargeability.

Electrostatic latent images are developed generally as follows; First, electrostatic latent images, which are positive electric charges or negative electric charges formed on a photosensitive member by various method, attract electrostatically a toner which is charged oppositely to electrostatic latent images to form toner images, and then the toner images are transferred electrostatically onto copying paper to fix the toner. Therefore, a toner should be charged to an adequate level to obtain clear copied images without fogs and the like. Further, the charge level should not change with time and environmental conditions. It is desired that the decrease of charge amount or the toner aggregation is not caused by, for example, humid changes, because the decrease of charge amount causes toner flying, resulting in fogs on a copying ground or the dirt inside a copying machine.

In order to overcome problems above mentioned, a charge controlling agent is generally added to a toner. In a color copy process which has become popular recently, white or light yellow charge controlling agents excellent in color-reproducibility are required.

With respect to negatively chargeable charge controlling agents, there are many kinds of white or light yellow charge controlling agents available in the market. They are highly effective for charge control and have not particular limitation to practical use. But, there are few kinds of positively chargeable charge controlling agents, in particular, which can be added to a color toner, except for colored nigrosine dyes, white quaternary ammonium salts or imidazoles (Japanese Patent Laid Open Nos. 287262/1987, 259265/1986, or 187350/1984).

A nigrosine dye is not a pure chemical compound, but a mixture of more than two kinds of chemical compounds. The precise composition of a nigrosine is unidentified. Therefore, the same degree of functions can not be always expected. A nigrosine dye works effectively to give stable electric charges to a toner when the toner is used in a copying machine at mediate or low copying speed. But, a nigrosine can not be applied similarly to a toner which is constituted of a resin of low melting point and low viscosity, and such a toner can not be used in a high speed copying machine. Further, a nigrosine dye can be hardly applied to a color toner because it is colored dye.

Quarternary ammonium salts are poor in environmental resistance of charging ability, big in particle size and have stinks. Further it does not melt at fixing temperature. Moreover, an ammonium salt is not so good in chargeability as well as a nigrosine dye.

With respect to imidazole compounds, diorganotin-bisimidazole (Japanese Patent Laid-Open No. 287262/1977) represented by the general formula below;

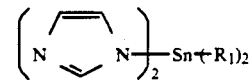

2-aminobenzimidazoles (Japanese Patent Laid-Open No. 217055/1986) represented by the general formula below:

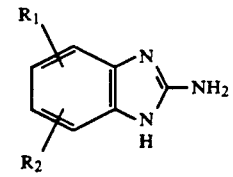

vinyl imidazole (Japanese Patent Laid-Open No. 187350/1984) represented by the general formula below;

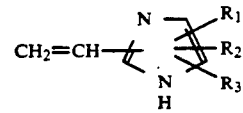

are known.

A charge controlling agent which is to be disclosed in the present invention is also an imidazole compound, but completely different in the structure from those above mentioned.

SUMMARY OF THE INVENTION

The object of the invention is to provide a positive charge controlling agent which effects to charge a toner positively, in particular, a colorless and white positive charge controlling agent suitable for a color toner.

Another object of the invention is to provide a positively chargeable toner excellent in electrification build-up properties, stability and environmental resistance.

Further object of the invention is to provide a positively chargeable toner excellent in color reproducibility and light-transmittance.

The present invention relates to a toner for developing electrostatic latent images comprising at least a resin a colorant, and an imidazole compound selected from the group consisting of an imidazole zinc complex represented by the general formula [I] below, an imidazole zinc compound represented by the general formula [II] below and an imidazole derivative represented by the general formula [III] below;

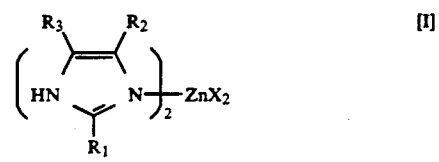

-continued

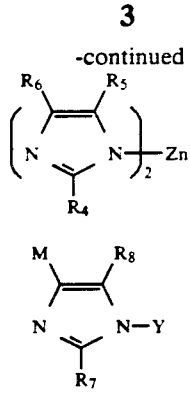
[II]

[III]

Wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, an aralkyl group or an aryl group; X represents a halogen atom, a hydroxy group or an ionic residual group of one valency; Y represents a hydrogen atom or a group represented by the formula [IV];

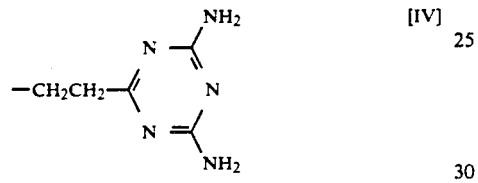
[IV]

M represents an hydrogen atom, an alkyl group, an aralkyl group, an aryl group, a group represented by the general formula [V] below;

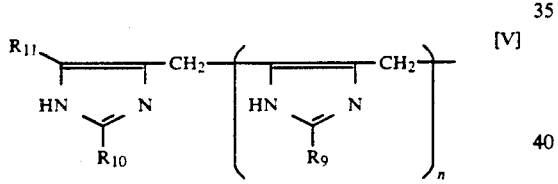
[V]

or a group represented by the general formula [VI];

[VI]

Wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1.

BRIEF DESCRIPTION OF THE DRAWING

FIG. 1 represents one of particle size distributions of particles prepared by suspension polymerization.

DETAILED DESCRIPTION OF THE INVENTION

This invention provides a positively chargeable toner excellent in electrification build-up properties, stability and environmental resistance, and that excellent in color reproducibility and translucence.

The objects of the invention can be achieved by incorporating specified imidazole compounds into a toner.

The present invention relates to a toner for developing electrostatic latent images comprising at least a resin, a colorant, and an imidazole compound selected from the group consisting of an imidazole zinc complex represented by the general formula [I] below, an imidazole zinc compound represented by the general formula [II] below:

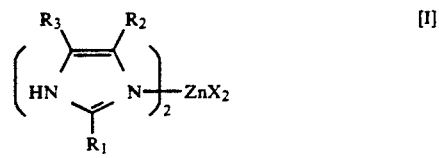
[I]

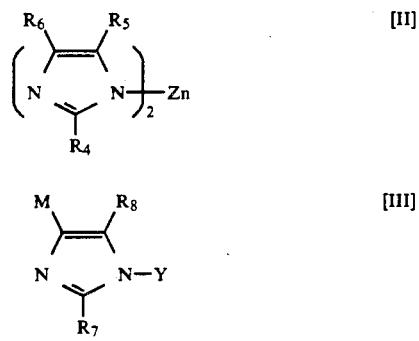
[II]

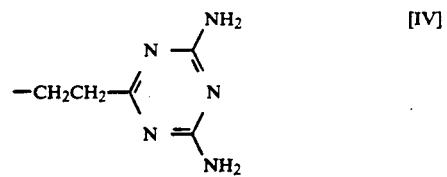
[III]

Wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, aralkyl group or an aryl group; X represents a halogen atom, a hydroxy group or an ionic residual group of one valency; Y represents a hydrogen atom or a group represented by the formula [IV];

[IV]

M represents an hydrogen atom, an alkyl group, an aralkyl group, an aryl group, a group represented by the general formula [IV] below;

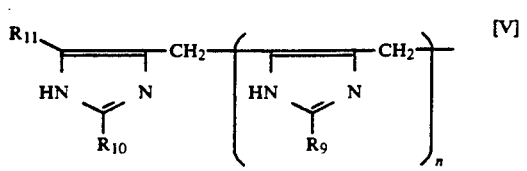
[V]

or a group represented by the general formula [IV];

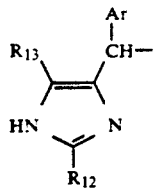

[VI]

Wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1.

The imidazole zinc complex [I], imidazole zinc compound [II], and imidazole zinc derivatives [III] are useful as charge controlling agent for a toner, in particular, a positive chargeable toner.

In the general formula [I], $R_1$ is a $C_1$-$C_{35}$ alkyl group (which may be branched), an aralkyl group such as benzyl and phenethyl, or an aryl group such as phenyl.

In the general formula [I], $R_2$ and $R_3$ are independently a hydrogen atom, a $C_1$-$C_{35}$ alkyl group (which may be branched), an aralkyl group such as benzyl or phenethyl or an aryl group such as phenyl.

X is a halogen atom, an ion residual group of one valence such as a nitric acid or acetic acid, or a hydroxy group.

An imidazole zinc complex represented by the general formula [I] can be synthesized as white powder by dissolving an imidazole compound and a zinc compound in an alcohol solvent such as methanol and ethanol or an aromatic solvent such as benzene and toluene to react them at refluxing temperature for 3-20 hours.

An imidazole zinc compound of the present invention represented by the general formula [I] are shown below, but they are shown with no significance in restricting the embodiment of the invention.

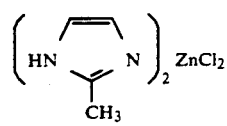
[I-1]

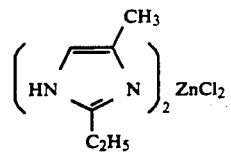
[I-2]

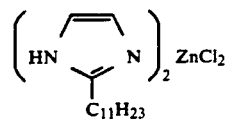
[I-3]

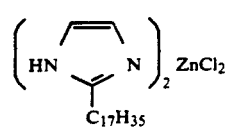
[I-4]

-continued

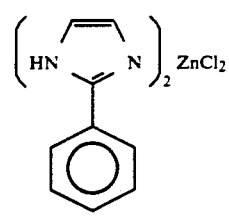
[I-5]

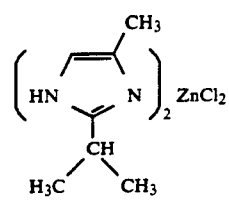
[I-6]

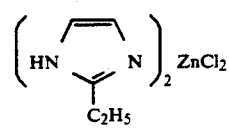
[I-7]

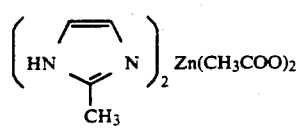
[I-8]

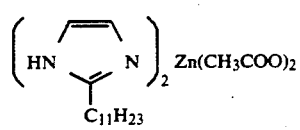
[I-9]

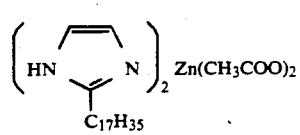
[I-10]

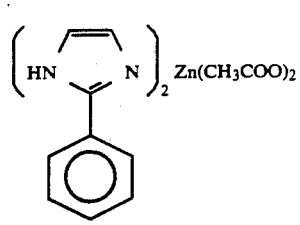
[I-11]

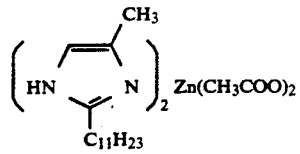
[I-12]

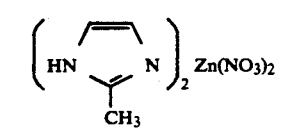
[I-13]

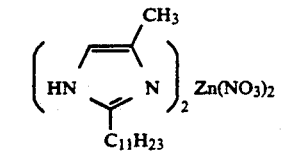
[I-14]

-continued

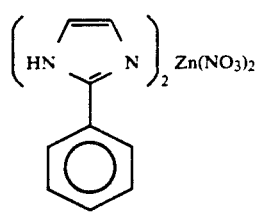 [I-15]

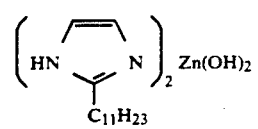 [I-16]

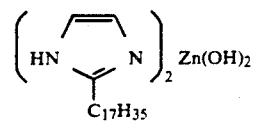 [I-17]

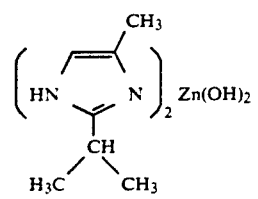 [I-18]

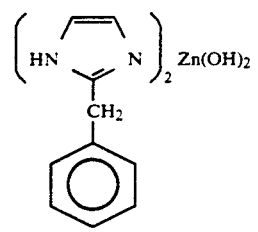 [I-19]

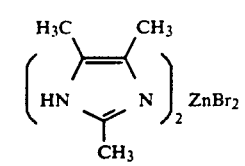 [I-20]

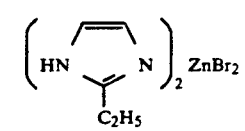 [I-21]

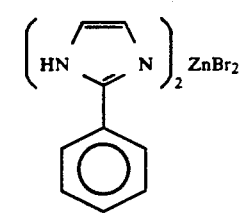 [I-22]

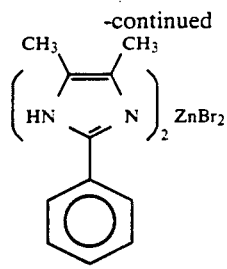 [I-23]

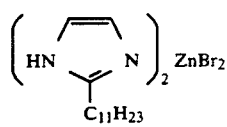 [I-24]

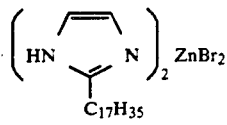 [I-25]

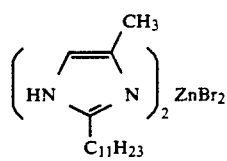 [I-26]

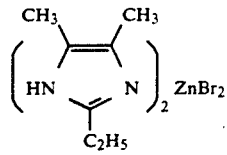 [I-27]

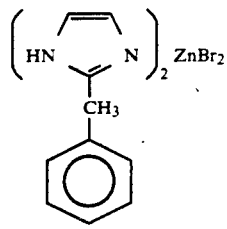 [I-28]

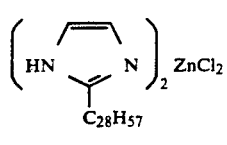 [I-29]

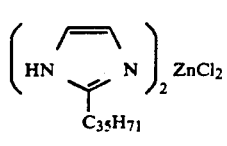 [I-30]

In the general formula [II], $R_4$ is a $C_1$–$C_{35}$ alkyl group (which may be branched), an aralkyl group such as benzyl and phenethyl, or an aryl group such as phenyl.

In general formula [II], $R_5$ and $R_6$ are independently a hydrogen atom, a $C_1$–$C_{35}$ alkyl group (which may be branched), an aralkyl group such as benzyl or phenethyl or an aryl group such as phenyl.

An imidazole zinc compound represented by the general formula [II] can be synthesized as white powder by dissolving an imidazole compound and a zinc chloride with a basic catalyst in an alcohol solvent such as methanol and ethanol or an aromatic solvent such as benzene and toluene to react them at refluxing temperature for 3-20 hours.
An imidazole zinc compound of the present invention represented by the general formula [II] are shown below, but they are shown with no significance in restricting the embodiment
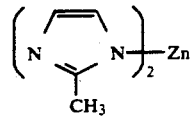
[II-1]
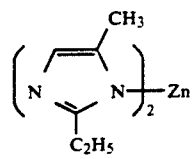
[II-2]
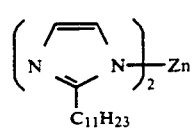
[II-3]
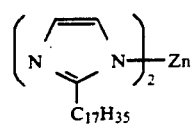
[II-4]
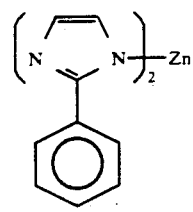
[II-5]
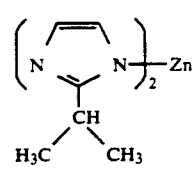
[II-6]
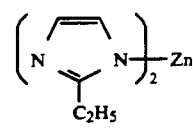
[II-7]
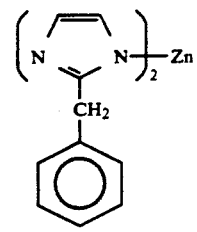
[II-8]
-continued
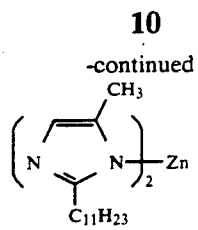
[II-9]
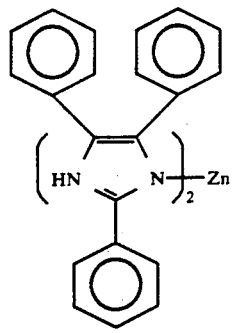
[II-10]
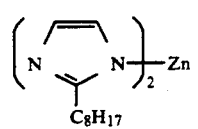
[II-11]
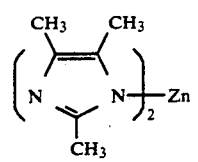
[II-12]
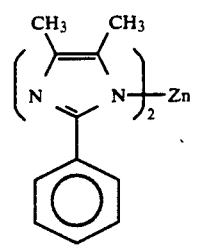
[II-13]
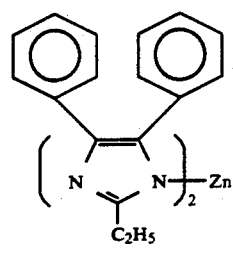
[II-14]
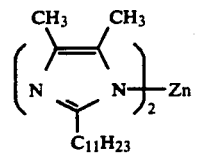
[II-15]
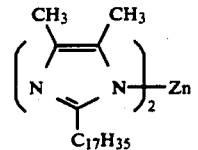
[II-16]

-continued

[II-17]
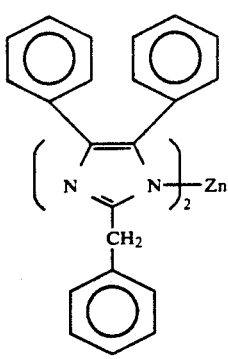

[II-18]
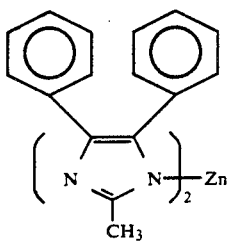

[II-19]
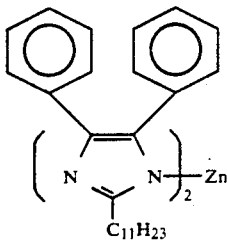

[II-20]
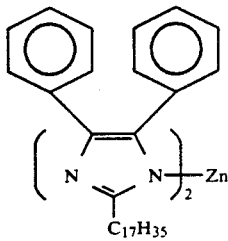

[II-21]
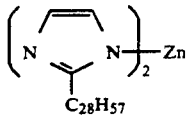

[II-22]
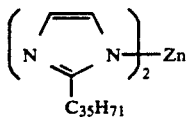

An imidazole compound represent by the general formula [III] is selected from the group consisting of imidazole derivatives represented by the general formula [VII] below;

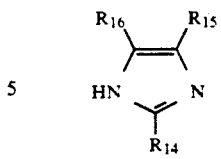

[VII]

wherein $R_{14}$ is a $C_8-C_{30}$ alkyl group; $R_{15}$ and $R_{16}$ are independently a hydrogen atom, a lower alkyl group, an aralkyl group, or an aryl group; an imidazole derivative represented by the general formula [VIII] below;

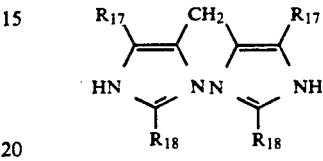

[VIII]

wherein $R_{17}$ and $R_{18}$ are independently an hydrogen atom, an alkyl group, an aralkyl group or an aryl group; an imidazole derivative represented by the general formula [IX] below;

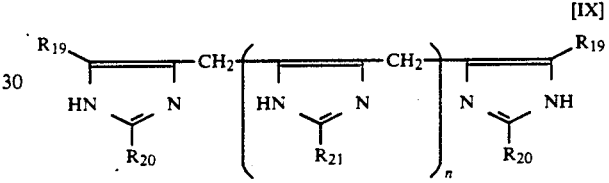

[IX]

wherein $R_{19}$, $R_{20}$ and $R_{21}$ are independently a hydrogen atom, an alkyl group or an aryl group; n is an integer of 1 or more;

an imidazole derivative represented by the general formula [X] below;

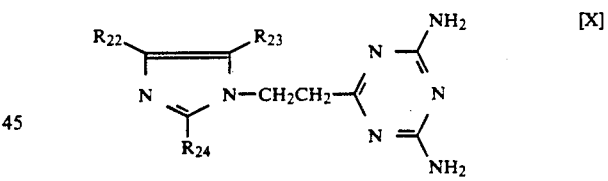

[X]

wherein $R_{22}$ and $R_{23}$ are respectively a hydrogen atom, an alkyl group, an aralkyl group or an aryl group which may have a substituent; $R_{24}$ is an alkyl group, an aralkyl group or an aryl group each of which may have a substituent; and an imidazole derivative represented by the general formula [XI] below;

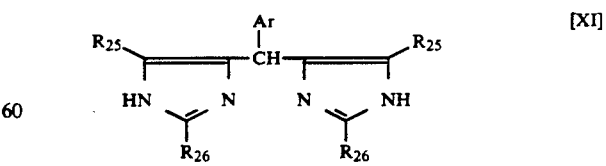

[XI]

wherein $R_{25}$ is an alkyl group; $R_{26}$ is an alkyl group, an aralkyl group or an aryl group, each of which may have a substituent; Ar is an aryl group or heterocyclic group, each of which may have a substituent.

In the general formula [VII];

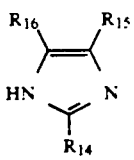  [VII]

wherein $R_{14}$ is a $C_8-C_{30}$ alkyl group; $R_{15}$ and $R_{16}$ are independently a hydrogen atom, a lower alkyl group, an aralkyl group, or an aryl group; an imidazole derivative represented by the general formula [VII] is per se known, and can be synthesized according to a generally known method, for example, described in Japanese Patent Publication No. 1548/1967.

An imidazole derivative represented by the general formula VII are shown below, but they are shown with no significance in restricting the embodiment;

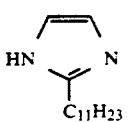  [VII-1]

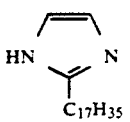  [VII-2]

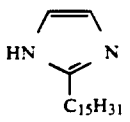  [VII-3]

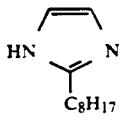  [VII-4]

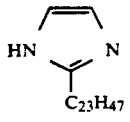  [VII-5]

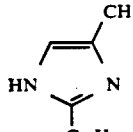  [VII-6]

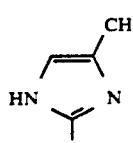  [VII-7]

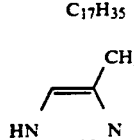  [VII-8]

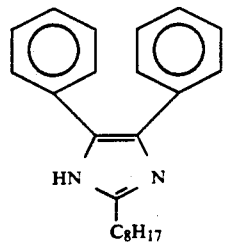  [VII-9]

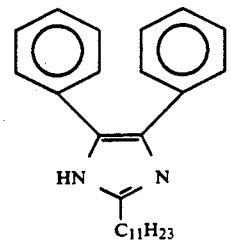  [VII-10]

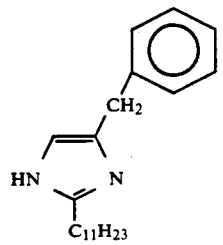  [VII-11]

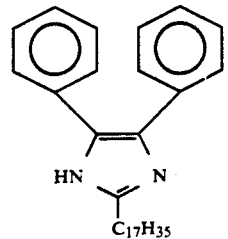  [VII-12]

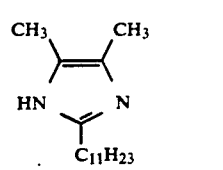  [VII-13]

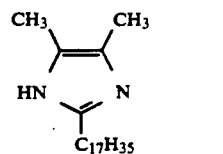  [VII-14]

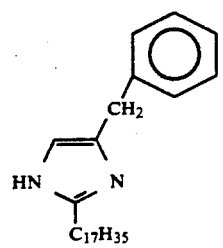  [VII-15]

-continued

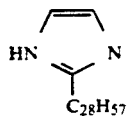  [VII-16]

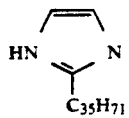  [VII-17]

In the general formula VIII;

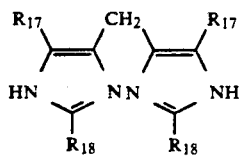  [VIII]

$R_{17}$ and $R_{18}$ are respectively a hydrogen atom, a $C_1$–$C_{35}$ alkyl group (which may be branched), an aralkyl group such as benzyl or phenethyl, or an aryl group such as phenyl.

An imidazole derivative represented by the general formula [VIII] can be synthesized easily be reacting an imidazole compound represented by the general formula [A] with formaldehyde directly or in the presence of inorganic catalyst of strong base in an adequate solvent as shown by reaction formula below.

A preferably solvent used in the synthesis is an alcohol such as methanol, ethanol, isopropanol, ethylene glycol, and ethylene glycol monoalkyl ether and the like. Reaction temperature depends on a kind of solvent but being in general within the range of 80°–200° C.

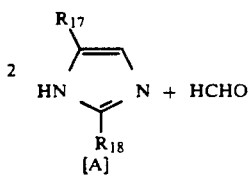

↓ a compound represented by the general formula[VIII]

An imidazole derivative represented by the general formula VIII are shown below, but they are shown with no significance in restricting the embodiment.

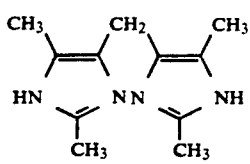  [VIII-1]

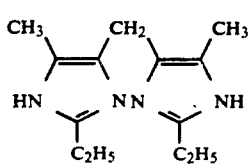  [VIII-2]

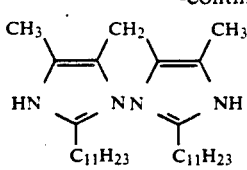  [VIII-3]

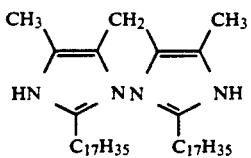  [VIII-4]

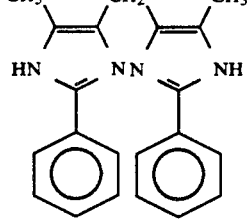  [VIII-5]

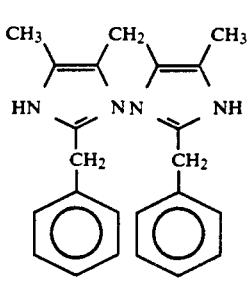  [VIII-6]

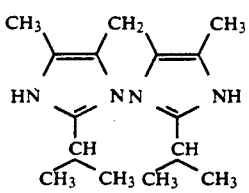  [VIII-7]

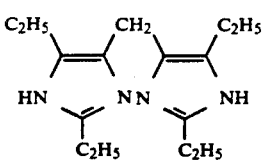  [VIII-8]

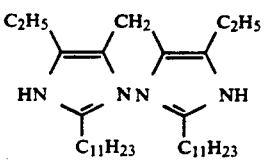  [VIII-9]

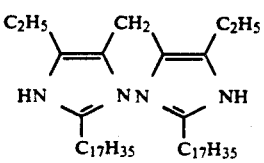  [VIII-10]

-continued

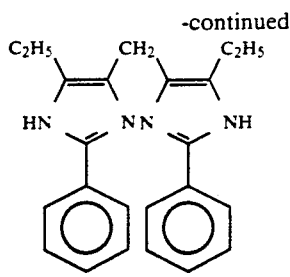

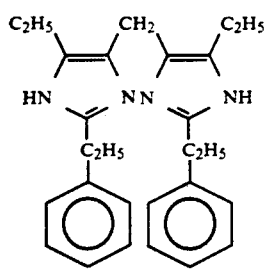

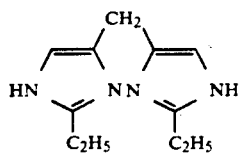

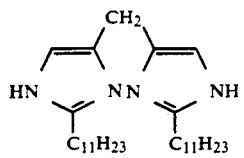

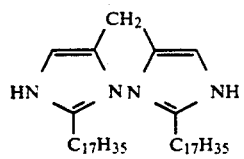

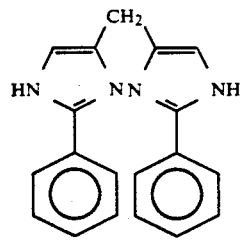

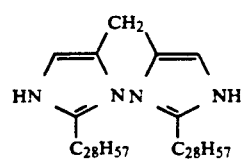

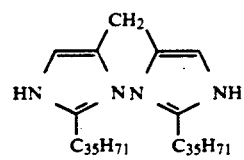

In general formula [IX]

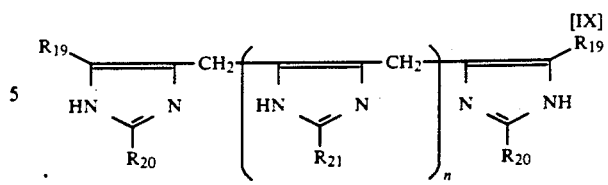

$R_{19}$, $R_{20}$ and $R_{21}$ are independently a hydrogen atom, a $C-C_{35}$ alkyl group (which may be branched), an aralkyl group such as benzyl and phenethyl, or an aryl group such as phenyl; n is an integer of 1 or more, preferably an integer of 1-50.

An imidazole derivative represented by the general formula [IX] can be synthesized easily by reacting an imidazole compound represented by the general formula [B] and an imidazole compound represented by the general formula [C] with formaldehyde directly or in the presence of inorganic catalyst of strong base in an adequate solvent as shown by reaction formula below.

A preferable solvent used in the synthesis is an alcohol such as methanol, ethanol, isopropanol, ethylene glycol, and ethylene glycol monoalkyl ether. Reaction temperature depends on a kind of solvent but being in general within the range of 80°-200° C.

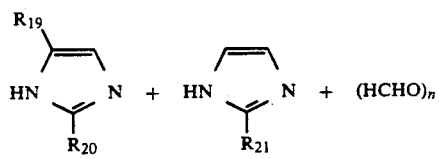

↓ a compound represented by the general formula [IX]

An imidazole derivative represented by the general formula [IX] are shown below, but they are shown with no significance in restricting the embodiment.

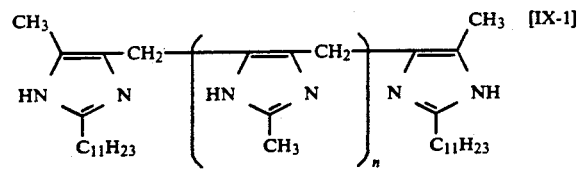

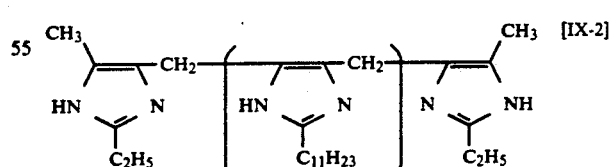

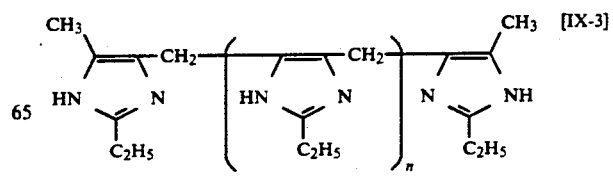

-continued

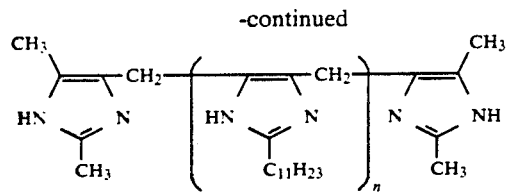  [IX-4]

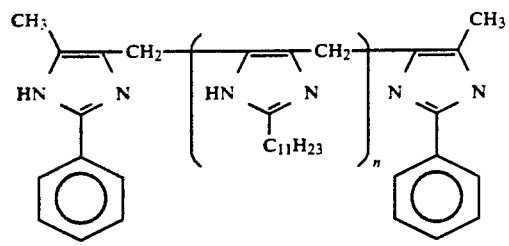  [IX-5]

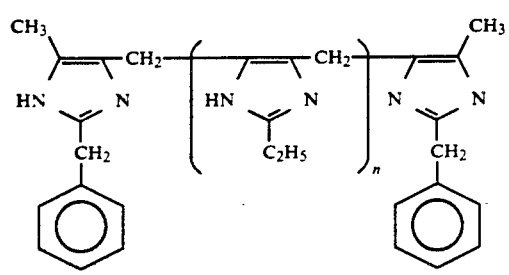  [IX-6]

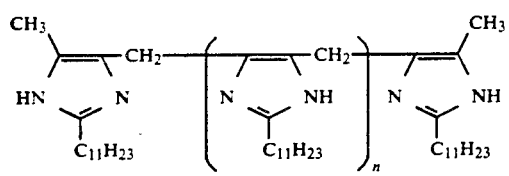  [IX-7]

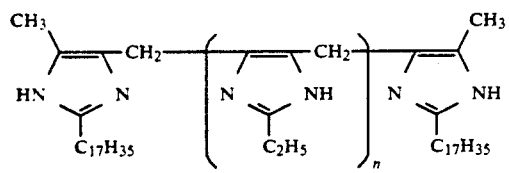  [IX-8]

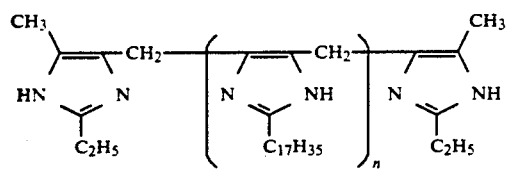  [IX-9]

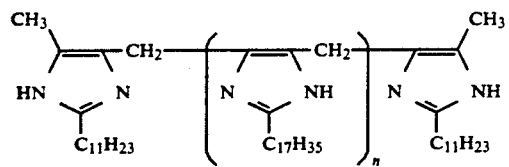  [IX-10]

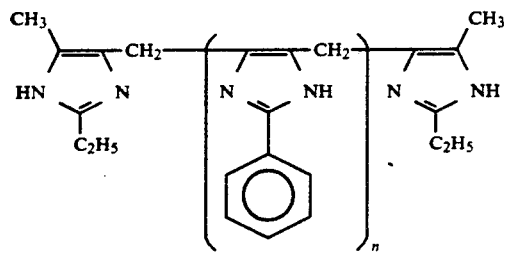  [IX-11]

-continued

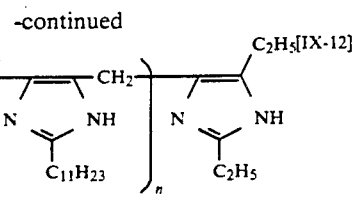  [IX-12]

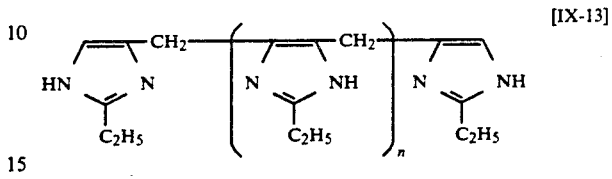  [IX-13]

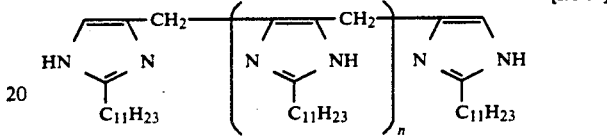  [IX-14]

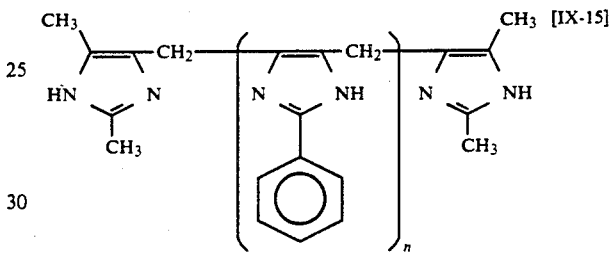  [IX-15]

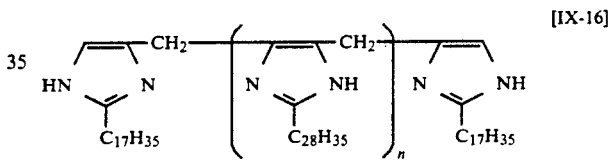  [IX-16]

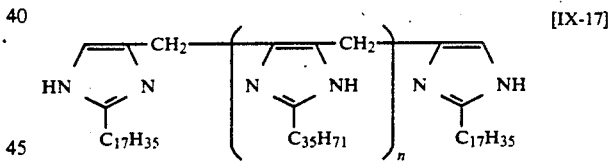  [IX-17]

In the general formula [X];

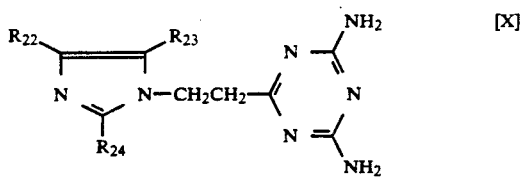  [X]

$R_{22}$ and $R_{23}$ are independently a hydrogen atom, a $C_1$–$C_{35}$ alkyl group (which may be branched), an aralkyl such as benzyl and phenethyl, or an aryl group such as phenyl, each of which may have a substituent.

$R_{24}$ is a $C_1$–$C_{35}$ alkyl group (which may be branched), an aralkyl group such as benzyl and phenethyl, or an aryl group such as phenyl, each of which may have a substituent.

An imidazole derivative represented by the general formula [X] can be synthesized as shown in the reaction formula below;

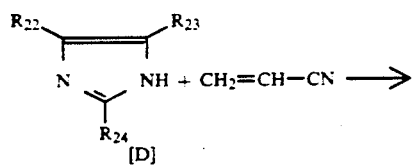

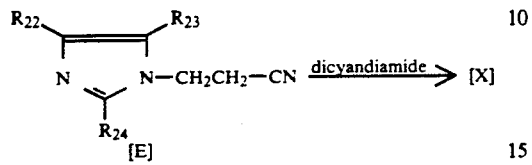

First, an imidazole compound of general formula [D] is reacted with acrylonitrile to obtain a compound represented by the formula [E], and then the compound of general formula [E] is reacted with dicyandiamide.

Some of imidazole derivatives of the formula [X] are known as curing agents for epoxy resin.

An imidazole derivative represented by the general formula [X] are shown below; but they are shown with no significance in restricting the embodiment.

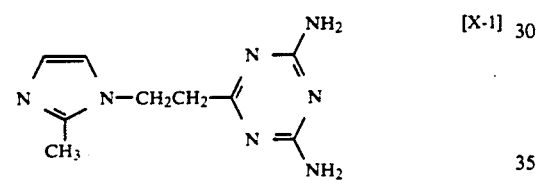

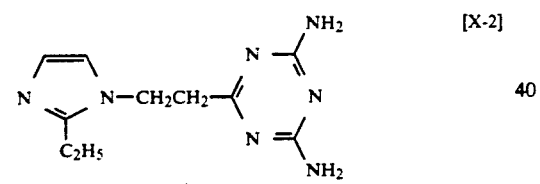

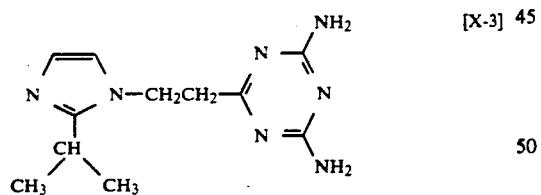

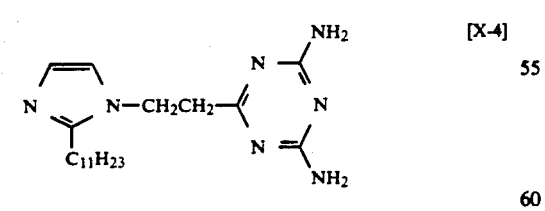

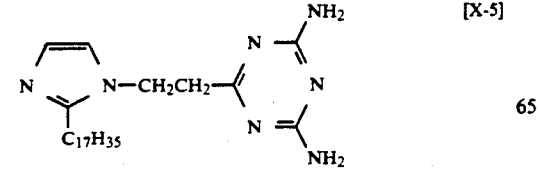

-continued

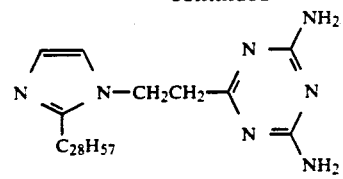

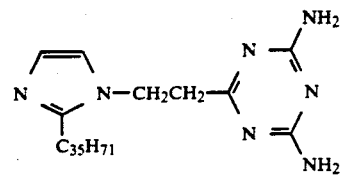

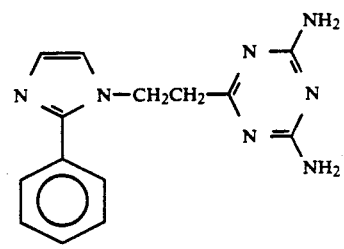

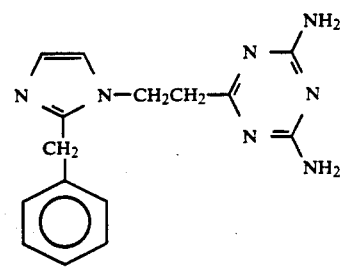

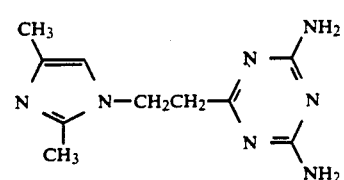

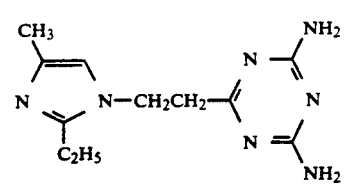

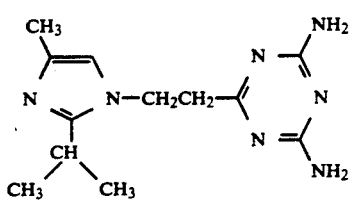

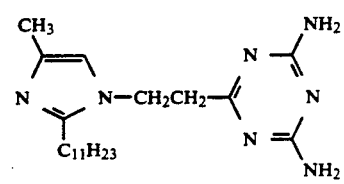

-continued
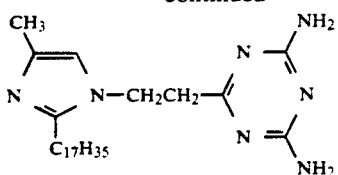
[X-14]
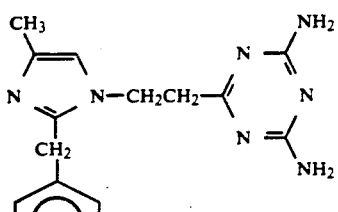
[X-15]
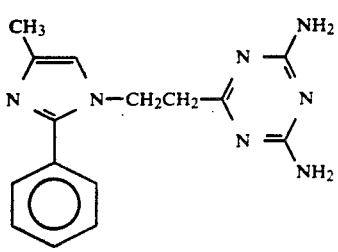
[X-16]
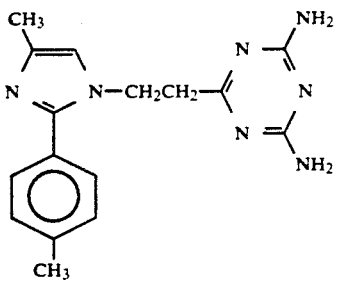
[X-17]
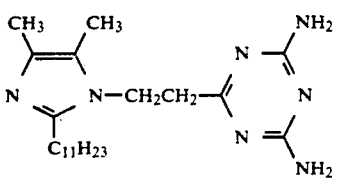
[X-18]
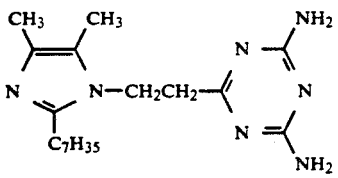
[X-19]
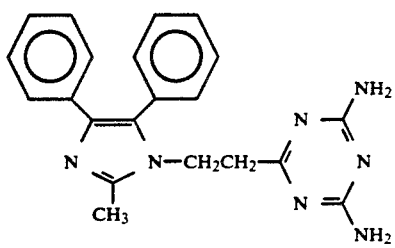
[X-20]
-continued
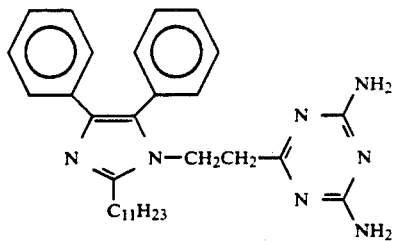
[X-21]
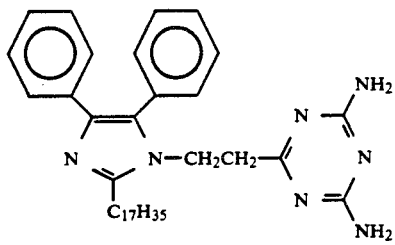
[X-22]
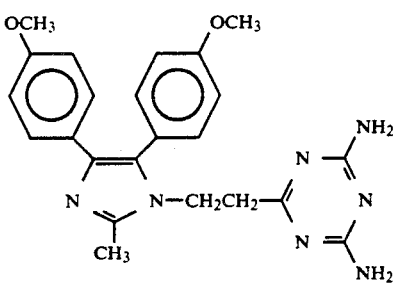
[X-23]
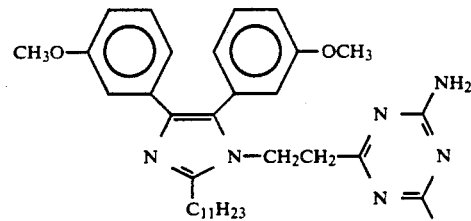
[X-24]
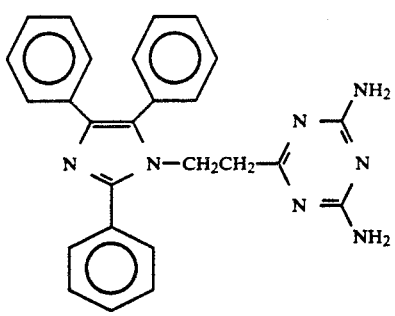
[X-25]
In the general formula [XI];
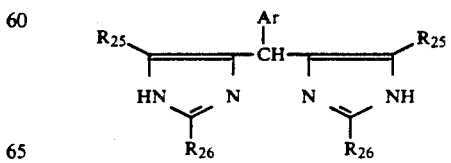
[XI]
$R_{26}$ is a $C_1$–$C_{35}$ alkyl group (which may be branched), an aralkyl group such as benzyl and phenethyl, or an aryl group such as phenyl; $R_{25}$ is a $C_1$-$C_{35}$ alkyl group (which may be branched); Ar is an aryl group such as phenyl, naphthyl, or a hetecocyclic group such as furan, thiophene and carbazole.

An imidazole derivative represented by the general formula [XI] can be synthesized by reacting an imidazole compound of general formula [F] with an imidazole compound of general formula [G] in the presence of alkali catalyst.

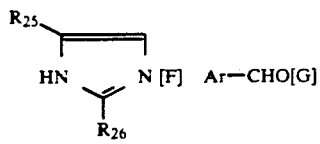

The reaction does not always requires a solvent, but, if necessary, preferable solvents are alcohols such as methanol and ethanol.

The reaction is carried out at the reaction temperature for 1-2 hours.

Preferable alkali catalysts are alkali hydroxide, particularly preferable ones are sodium hydroxide and potassium hydroxide.

An imidazole derivative represented by the general formula [XI] are shown below, but they are shown with no significance in restricting the embodiment.

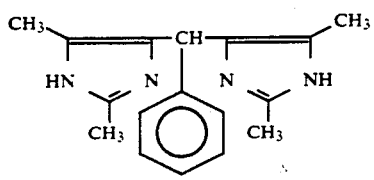

[XI-1]

[XI-2]

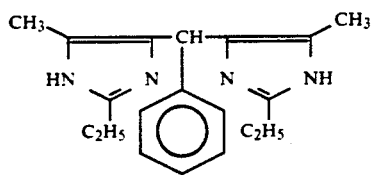

[XI-3]

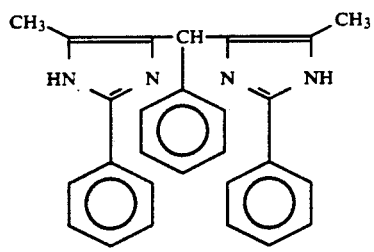

[XI-4]

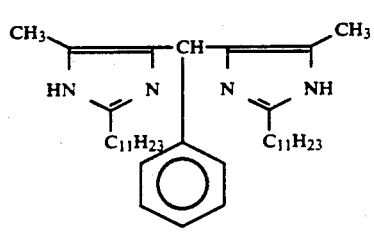

[XI-5]

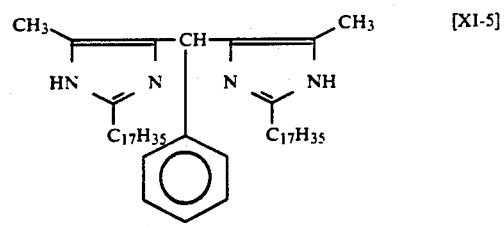

[XI-6]

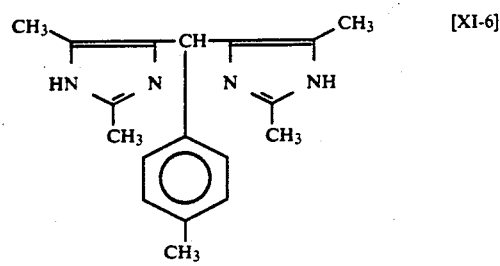

[XI-7]

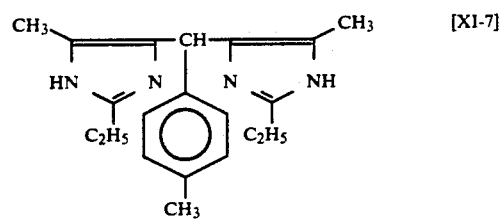

[XI-8]

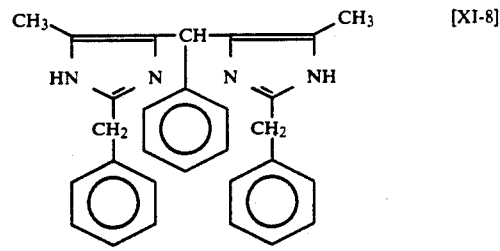

[XI-9]

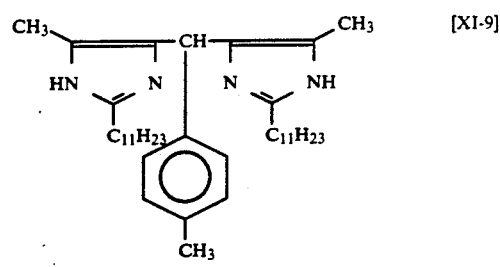

[XI-10]

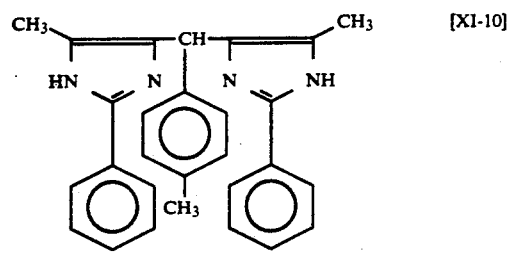

-continued
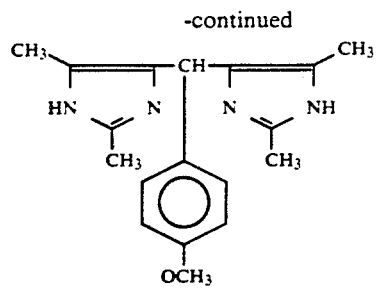 [XI-11]
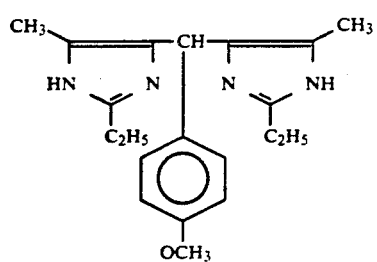 [XI-12]
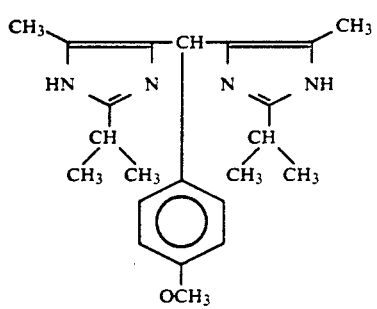 [XI-13]
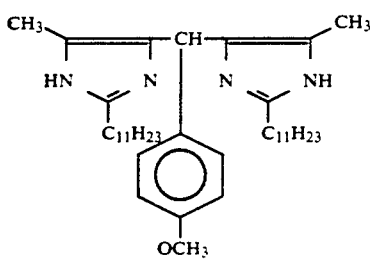 [XI-14]
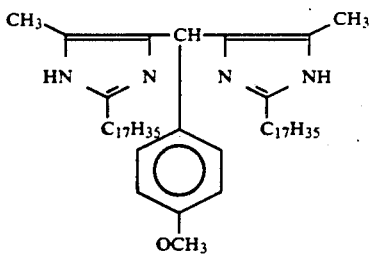 [XI-15]
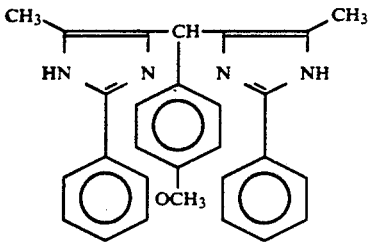 [XI-16]
-continued
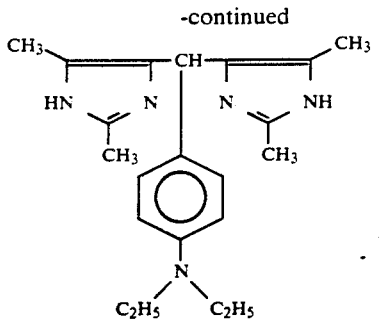 [XI-17]
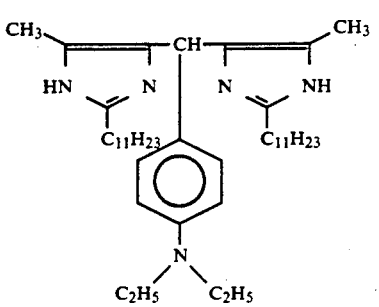 [XI-18]
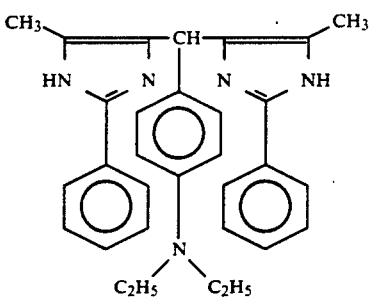 [XI-19]
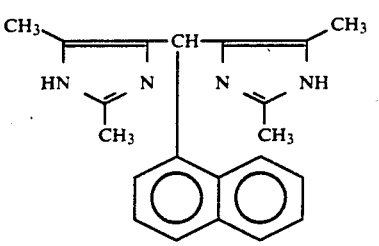 [XI-20]
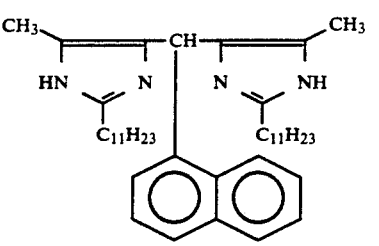 [XI-21]
[XI-22]

-continued
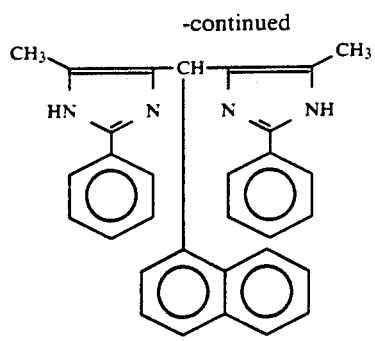 [XI-23]
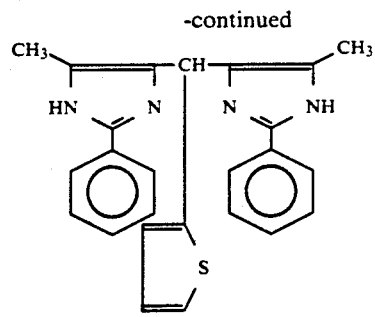 [XI-30]
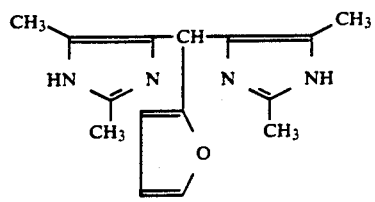 [XI-24]
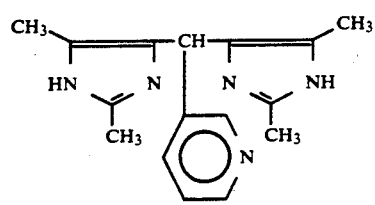 [XI-31]
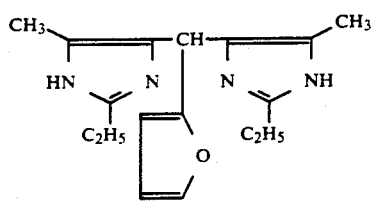 [XI-25]
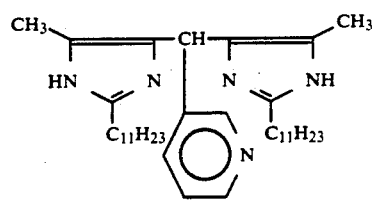 [XI-32]
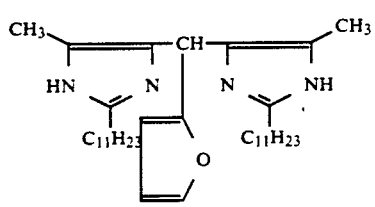 [XI-26]
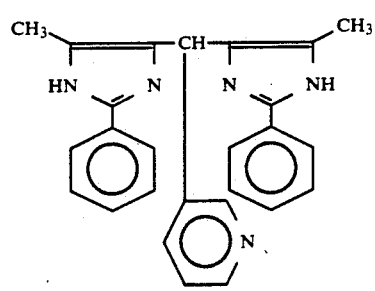 [XI-33]
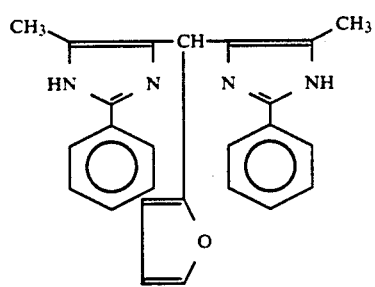 [XI-27]
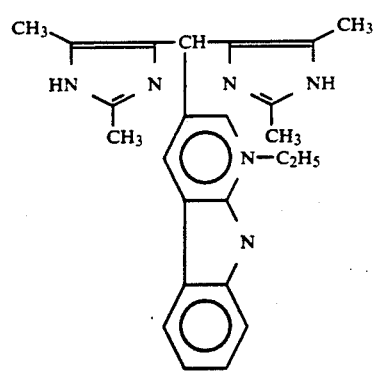 [XI-34]
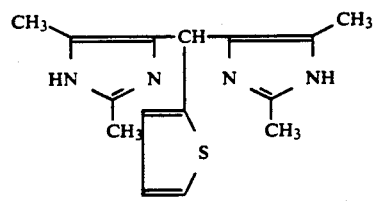 [XI-28]
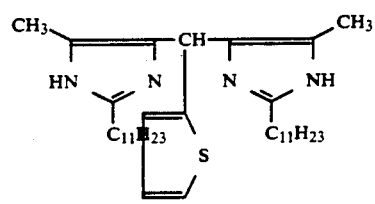 [XI-29]
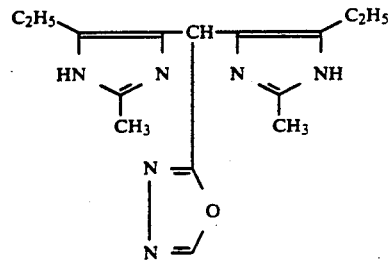 [XI-35]

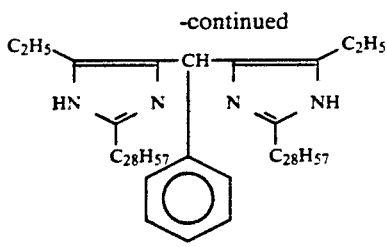

[XI-36]

Further the combination of homopolymer of a nitrogen-containing vinyl-monomer represented by the general formula [XII] or copolymer thereof with styrene (referred to as "charge controlling agent of [XII]" hereinafter with imidazole charge controlling agents represented by the general formula [I]–[III]) achieves the further improvement in heat resistance.

$$CH_2=\underset{\underset{COL+CH_2\overline{)_m}N\underset{R_{29}}{\overset{R_{28}}{\diagup}}}{|}}{\overset{R_{27}}{C}} \quad [XII]$$

wherein $R_{27}$ is a hydrogen atom or a methyl group, $R_{28}$ and $R_{29}$ are independently a $C_1$–$C_4$ alkyl group; L is an oxygen atom or an imino group; m is an integer of 1–4.

The combination above mentioned effects the improvement of charging level and stability of chargeability, and the adjustment of the addition amount of charge controlling agents makes it possible to charge polyester resin positively although polyester resin has relatively high acid value and poor positive charging properties.

A nitrogen containing vinyl monomer represented by the general formula [XII] is shown below; but they are shown with no significance in restricting the embodiment.

amino(metha)acrylic monomers (which means aminoacrylic monomers and aminomethacrylic monomers, same hereinafter) such as N,N-dimethylaminomethyl(metha)acrylate, N,N-diethylaminomethyl(metha)acrylate, N,N-dimethylaminoethyl(metha)acrylate, N,N-diethylaminoethyl(metha)acrylate, N,N-dimethylaminopropyl(metha)acrylate, N,N-dimethylaminobutyl(metha)acrylate and the like;

Amino(metha)acrylamides such as N,N-dimethylaminoethyl(metha)acrylamide, N,N-diethylaminoethyl(metha)acrylamide, N,N-dimethylaminopropyl(metha)acrylamide, N,N-diethylaminopropyl(metha)acrylamide and the like.

The copolymerization ratio of a nitrogen containing vinyl monomer to a styrene monomer is not particularly limitative, but preferably 100:1–1:99 in molar ratio. The bigger, the ratio of nitrogen containing vinyl monomer is, the less, the usage of the copolymer is. But, when considering heat resistance of a toner, styrene should be copolymerized with nitrogen containing vinyl monomer because the copolymer is required to have glass transition temperature of 50° C. or more. The glass transition temperature can be adjusted by the styrene content. Anyway, the copolymerization ratio may be determined considering the usage of charge controlling agents and working properties for grinding.

A copolymer aforementioned can be prepared by known methods such as solution polymerization, bulk polymerization and the like. The preferred method is solution polymerization because the exotherm can be controlled easily. In the solution polymerization, solvents are not limitative, so far as they are inactive against monomers. Preferred solvents are benzene, toluene, xylene and the like.

Charge controlling agents represented by the general formula [I]–[III] and [XII] can be applied to toners per se known such as a toner prepared by grinding method, a capsule toner and the like. The charge controlling agents of [I]–[III] and [XII] may be incorporated into a toner or adhered and fixed on the furface of a toner particle.

When a charge controlling agent is incorporated into a toner, it may be added together with additives such as colorants according to usual preparation methods such as grinding method, encapsulating method. On the case of a capsule toner, it is desirable a charge controlling agent is contained at outer layer of the toner.

When a charge controlling agents is adhered and fixed on the surface of a toner, the charge controlling agent is adhered on the surface of a toner with the help of van der Waals force, electrostatic force on the like.

Suitable machines for adhering and fixing a charge controlling agent on the surface of a toner are not limitative but preferably exemplified by Hybridization system (made by Nara Kikai Seisakusho K.K.), (which applies impacts in high speed air current), Angmill (made by Hosokawa Micron K.K.), Mechanomill (made by Okada Seiko K.K.) and the like.

The content of a charge controlling agent should be adjusted depending on kinds of toners, additives, binding resin or the like, or developing systems of toners (a two components system or a single component system). When a charge controlling agent is incorporated into a toner, it is contained at the content of 0.1–20 parts by weight, preferably 1–10 parts by weight on the basis of 100 parts by weight of a toner constituting resin. If it is less than 0.1 part by weight, desired charge amount can not be achieved. If it is more than 20 parts by weight, unstable charge amount causes the deterioration of fixing properties.

When a charge controlling agent is used by adhering and fixing on the surface of toner particles, it is contained at the content of 0.001–10 parts by weight, preferably 0.05–2 parts by weight,, more preferably 0.1–1 part by weight on the basis of 100 parts by weight of toner particles. If it is less than 0.001 part by weight, charge amount becomes insufficient because there exist little amount of charge controlling agent on the surface of toner particles. If it is more than 10 parts by weight, particles of charge controlling agents do not adhere completely on the surface of toner particles resulting in such a problem that the particles of charge controlling agent separate from the surface of toner particles.

When a charge controlling agent is adhered and fixed on the surface of toner particles, it can provide a toner with stable charging properties with only a little usage as above mentioned. Moreover, because a charge controlling agent of the present invention is white, a toner which is excellent in chargeability and can form clear color-copied images can be prepared.

The size of charge controlling agent of [I]–[III] or [XII] is 5 μm or less, preferably 3 μm or less, more preferably 1 μm or less when the charge controlling agent is incorporated into a toner. If the size is more than 5 μm, the charge controlling agent can not disperse uniformly and charging properties become unbalanced. When a charge controlling agent is adhered and fixed on the surface of toner particles, the size of charge controlling agent is 1 μm or less, more preferably 0.5 μm. If it is more than 0.5 μm, it becomes difficult for the particles of charge controlling agents to adhere to surfafe of toner particles.

When a charge controlling agent of [I]–[III] is used in combination with a charge controlling agent of [XII], the mixing ratio thereof should be adjusted depending on charging level, glass transition temperature of a developer, stability of charging properties and the like, but may be in general 1:9–9:1, preferably 1:5–5:1. An imidazole agent of [I]–[III] effects more improvement in charging level than a charge controlling agent of [XII].

With respect to a resin constituting a toner, it is not limitative and any binder resin for a toner can be used, being exemplified by thermoplastic resins such as styrene resins, (metha)acrylic resins, olefin resins, amide resins, carbonate resins, polyether, polysulfone, polyester resins, and epoxy resins; thermosetting resins such as urea resins, urethane resins, and epoxy resins, copolymers thereof, or a blend thereof. Further, an oligomer or a prepolymer of the thermosetting resins may be used. A mixture of the oligomer or the prepolymer with the resins above mentioned or a crosslinking agent may be used.

A resin for a toner may be prepared by any method such as solution polymerization, suspension polymerization, emulsion polymerization and the like. But, in general, a polymer prepared by suspension polymerization has broad distribution in particle size and being not suitable for a positively chargeable color toner. Even if a binder resin of a toner is the one prepared by suspension polymerization, the present invention can provide a toner excellent in positively chargeable properties and copied image formation properties without toner flying and fogs in the combination of suspension-polymerized polymer with a charge controlling agent of [I]–[III] or [XII], in which the content of particles of 150 mesh or finer and that of 16 mesh or rougher is adjusted to specified degree, and the ratio of average volume size to number average size is adjusted to specified range. Hereinafter, suspension polymerized polymers more suitable for the present invention are explained.

Raw materials for the production of suspension polymerization resin to which the present invention can be applied are exemplified by monofunctional vinyl monomers such as styrene monomers such as styrene, α-methylstyrene, p-methylstyrene(vinyltoluene), p-butyl styrene and p-chlorostyrene; (metha)acrylic monomers (which means metacrylic monomers and acrylic monomers, same hereinafter) such as (metha)acrylic acid, methyl(metha)acrylate, ethyl(metha)acrylate, propyl(metha)acrylate, butyl(metha)acrylate, pentyl(metha)acrylate, hexyl(metha)acrylate, heptyl(metha)acrylate, octyl(metha)acrylate, nonyl(metha)acrylate, decyl(metha)acrylate, undecyl(metha)acrylate, dodecyl(metha)acrylate, glycidyl(metha)acrylate, methoxyethyl(metha)acrylate, propoxyethyl(metha)acrylate, butoxyethyl(metha)acrylate, methoxydiethyleneglycol(metha)acrylate, methoxyethyleneglycol(metha)acrylate, methoxydibutoxytriethyleneglycol(metha)acrylate, methoxydipropyleneglycol(metha)acrylate, phenoxyethyl(metha)acrylate, phenoxydiethyleneglycol(metha)acrylate, phenoxytetraethyleneglycol(metha)acrylate, benzyl(metha)acrylate, cyclohexyl(metha)acrylate, tetrahydrofurfuryl(metha)acrylate, dicyclopentenyl(metha)acrylate, dicyclopentenyloxyethyl(metha)acrylate, (metha)acrylic acid-N-vinyl-2-pyrrolidone, (metha)acrylonitrile, (metha)acrylamide, N-methylol(metha)acrylamide, 2-hydroxyethyl(metha)acrylate, hydroxypropyl(metha)acrylate, hydroxydibutyl(metha)acrylate, 2-hydroxy-3-phenyloxypropyl(metha)acrylate, diacet(metha)acrylamide; vinylpyridine, a mixture thereof, and the like. Polyvinylmonomers such as divinylbenzene, a reaction product of polyol with (metha)acrylic acid such as ethyleneglycol di(metha)acrylate, 1,3-butyleneglycol di(metha)acrylate, 1,4-butanediol di(metha)acrylate, 1,5-pentanedioldi(metha)acrylate, 1,6-hexanediol di(metha)acrylate, neopenthylglycol di(metha)acrylate, diethyleneglycol di(metha)acrylate, triethyleneglycol di(metha)acrylate, polyethyleneglycol di(metha)acrylate, tripropyleneglycol di(metha)acrylate, hydroxypivalic acid-neopentylglycolate-di(metha)acrylate, trimethylolethane-tri(metha)acrylate, trimethylolpropane-tri(metha)acrylate, pentaerythritol-tri(metha)acrylate, pentaerythritol-tetra(metha)acrylate, tris(metha)acryloxyethylphosphate, bis((metha)acryloyloxyethyl)hydroxyethyl isocyanurate or tris((metha)acryloyloxy ethyl)isocyanurate; half-esterification compounds of glycidyl(metha)acrylate and (metha)acrylate; may be used as a comonomer at the content of 0–20 percents by weight on the basis of total weight of monomers.

An initiator of suspension polymerization for the production of suspension polymer resin is exemplified by a radical initiator of peroxides such as benzyl peroxide, lauryol peroxide, octanoyl peroxide, decanyol peroxide, 2,4-dichlorobenzoyl peroxide, isobutyryl peroxide, 3,3,5-trimethylhexanoyl peroxide, acetyl peroxide, succinyl peroxide, 3,3,5-trimethylcyclohexanone ditertiarylbutyl peroxyketal, cyclohexanone ditertiarybutyl peroxyketal, methyl ethyl ketone ditertiarybutyl peroxyketal, methyl hexyl ketone ditertiarybutyl peroxyketal, or the like; and azobis compounds such as 2,2'-azobisisobutyronitrile, 2,2'-azobis(2,4-dimethylvaleronitrile), 2,2'-azobis(4-methoxy-2,4-dimethylvaleronitrile), 2,2'-azobis-methyl butylate, 1,1'-azobis(cyclohexanane-1-carbonitrile) or like. Among these initiators, diacyl peroxides and peroxy ketals are preferably. The usage of an initiator is 0.01–20 wt.%, preferably 0.1–5 wt% on the basis of total weight of monomers.

A molecular weight modifier for radical polymerization may be also used. They are exemplified by mercaptans such as butyl mercaptan, octyl mercaptan, dodecyl mercaptan, methyl-2mercaptopropionate, ethyl-2-mercaptopropionate, butyl-2-mercaptopropionate, octyl-2-mercaptopropionate, pentaerythritol tetra(2-mercaptopropionate), ethylene glycol di(2-mercaptopropionate), glycerine tri(2-mercaptopropionate); halogenated hydrocarbons such as chloroform, bromoform, tetrabromocarbon and the like, Such a molecular weight modifier is used at the ratio of 0–3 percents by weight on the basis of total weight of vinyl monomers.

A suspension polymerization, a dispersant is added, which is exemplified by a water-soluble polymeric dispersant such as partially saponified polyvinyl alcohol, alkylcellulose, hydroxy-alkylcellulose, carboxyalkylcellulose, polyacrylamide, polyvinylpyrrolidone, polyacrylic acid and an alkali metal salt thereof, polymethacrylic acid and an alkali metal salt thereof, or the like; a water-insoluble inorganic dispersant such as pottasium phosphate, hydroxy apatite, magnesium phosphate, magnesium pyrophosphate, calcium carbonate, barium sulfate, hydrophobic silica or the like. A water soluble dispersant is added to aqueous solvent at the ratio of 0.0001–5 persents by weight to aqueous solvent, and a water soluble inorganic dispersant is added to aqueous solvent at the ratio of 0.01–15 percents by weight to aqueous solvent. Stable dispersion can not obtain in too small amount of dispersant, while dispersion effects are overachieved by too much amount of dispersant.

A mixture of vinyl monomers as aforesaid with polymerization-initiator is added to water containing a dispersant, stirred for dispersion and heated to initiate suspension polymerization. The polymerization temperature is most preferably 10°–20° C. higher than the temperature at which half amount of the polymerization initiator is digested for 10 hours. A polymerization initiator may be added at one time or dividedly in the polymerization process. Afterr polymerization, the polymerized vinyl monomers are dehydrated and dried in an usual manner.

One kind of suspension polymerized resin above mentioned may be used. More preferably, a mixture of low molecular weight vinylpolymer and high molecular weight vinylpolymer is used. The mixture may be produced by producing low molecular weight vinylpolymer and high molecular weight vinylpolymer separately and then mixing the two polymers. In other method, first, one vinylpolymer is produced and then the other vinylpolyer is produced in the same reaction system. The latter production method of a mixture of low and high molecular weight vinylpolymers may achieve uniform mixing and dispersion of the two polymers, which effects excellent copied image properties, simplification of toner production method, and low production cost.

A mixture of low and high molecular weight vinylpolymers is prepared desirably such that the ratio of low molecular weight vinylpolymer to high molecular weight vinylpolymer is 5/95–95/5. If the ratio is too small, the fixing properties of a toner become poor. If the ratio is too high, the off-set resistant properties of a toner become poor.

Low molecular weight vinylpolymer is preferably adjusted to have 1500–100000 in weight-average molecular weight (Mw), 1000–20000 in number-average molecular weight (Mn) and 55°–80° C. in glass transition temperature (Tg). If low molecular weight vinylpolymer has too high average molecular weight (Mw, Mn), fixing properties of a toner become poor. If low molecular weight vinylpolymer has too small average molecular weight, toner fogs are caused. If the glass transition temperature is too low, blocking-resistant properties of a toner become poor. If the glass transition temperature is too high, fixing properties of a toner become poor.

A mixture of low molecular weight vinylpolymer with high molecular weight vinylpolymer is preferably adjusted to have 100000–500000 in weight-average molecular weight and 50°–75° C. in glass transition temperature so that copied image properties may be balanced.

Weight-average molecular weight and number-average molecular weight in the present invention are measured by gel permeation chromatography on the basis of the culibration curve of standard polystyrene. Glass-transition temperature is measured by differential scanning calorimeter (DSC) to show the temperature of maximum point of endotherm accompanied by glass transition.

The particle size distribution of suspension-polymerized particles is generally broad although mean particle size may be controlled by adjusting stirring power, ratio of water to monomers, kind and amount of dispersants.

In the present invention, suspension polymerized resin is sifted so that the resin particles of finer than 150 meshes may be 1 percent by weight or less, the resin particles of 32–150 meshes may be 78 percents by weight or more and the resin particles of rougher than 16 meshes may be 1 perent by weight or less, and that the ratio of average volume size (Dv) to number average size (D$_1$) may be preferably within the range between 1.04 and 1.40. If the ratio is less than 1.04, there arise such problems as poor dispersibility of pigments, much toner flying, many fogs and the like. If the ratio is more than 1.40, there also arises such a problem of fogs in copied images and the like.

In general, a toner is prepared by mixing uniformly all raw materials including suspension polymerized polymer and other additives such as pigments and grinding them finely in, fox example, henschel mixer, super mixer, ribbon blender or ball mills. In order to mixing raw materials of a toner uniformly, size distribution of each particle of raw materials is preferably as narrow as possible. Particles of suspension polymerized polymer are hardly ground in an usual grinder, and so suspension polymerized particles containing many big particles (rougher than 16 meshes) prevent additives such as a charge controlling agent and a colorant from dispersing uniformly with a kneader or an extruder, resulting in much toner flying and many fogs in copied images.

Further, it has been found that residues after reaction such as decomposed residue of catalysts, dispersants, monomers and oligomers are lible to be incorporated into fine particles of suspension polymerized polymer. These residues act as plasticizers, resulting in much weight loss of toner by heating, the deterioration of heat resistance (decrease of Tg) and charging stability, fogs or toner flying. In order to avoid these influences, it is necessary to reduce suspension polymerized particles of finer than 150 meshes to the content of 1 percent by weight or less. Moreover, those residues after reaction can not be washed away, therefore it is necessary to reduce small particles of finer than 150 meshes.

By the way, the present invention adopts screen openings of Tyler in mesh. Average volume size (Dv) is defined by the formula (XIII) below;

$$\dot{D}v = (\epsilon n d^3 / \epsilon n)^{1.66} \tag{XIII}$$

wherein n is the number of particles; d is particle size. Number average size D$_1$ is defined by the formula (XIV) below;

$$\dot{D}_1 = \epsilon n d / \epsilon n \tag{XIV}$$

wherein n and d are same as those of the formula (XIII). Particle size may be measured by a method per se known, such as Coulter counter, Microtruck, centrifuge sedimentation, photomicrograph, sieve analysis and the like so far as it can be measured accurately and in good reproducibility. The present invention adopts easy sieve analysis because relatively big particles are used.

Sieve analysis is carried out below; percents by weight of resin particles left on the sieve openings of 8, 9, 10, 12, 14, 16, 20, 24, 28, 32, 35, 42, 48, 60, 65, 100, 150, 200 are calculated respectively. The particle size distribution is graphed in the cordinate system with ordinate axis of the percents by weight and abscissa axis of mesh in lagarithmx scale. Mean particle size (d$_{50}$) corresponds to 50 % in cumulative distribution.

In FIG. 1, the particle size distribution of suspension polymerized polymer prepared in synthetic example 5 of suspension polymerized polymer discribed later is shown according to the sieve analysis above mentioned.

When suspension polymerized polymer is used as a binder resin of a toner, it is contained at 88–99 percents by weight, preferably 90–95 percents by weight. If the content is less 88 percents by weight, heat resistance becomes insufficient and fixing properties of toner become poor. If the content is more 99 percents by weight, charge amount becomes insufficient.

A toner constituted mainly by suspension polymerized polymer is prepared such that decomposed residues of catalyst such as carboxylic acids, ketones or the like is 0.1–1 percent by weight respectively. Carboxylic acids are decomposed residues of diacyl peroxides used as polymerization initiators in the preparation of low molecular weight vinyl polymer. Ketones are decomposed residues of peroxyketals used as polymerization initiators in the preparation in high molecular weight vinyl polymer. Other decomposed components of polymerization initiators (for example, alcohols such as t-butanol) are removed easily in the processes of dehydration, drying, toner-production. Decomposed residues such as carboxylic acid, ketones or the like include those contained in other componnts (for example, charge controlling agent of formula [XII] prepared by suspension polymerization). If the decomposed residues are less than 0.1 percent by weight, good positive chargeability cannot be achieved. If the decomposed residues are more than 1 percent by weight, they act as a plasticizer, resulting in poor heat resistance and poor preservation stability. The amount of decomposed residues such as carboxylic acids and ketones can be adjusted by polymerization conditions, usage of polymerization initiator, washing of polymer particles, melting and kneading time, or the like.

The amount of decomposed residues of polymerization initiators contained in a toner can be analyzed with gass chromatography and the like.

Monomers constituting general resins for toners other than the aforemmentioned monomers for suspension polymerization are exemplified by; styrenes and derivatives thereof such as o-methylstyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, 3,4-dichlorostyrene, halogenated vinyl monomers such as vinyl chloride, vinylidene chloride, vinyl bromide, vinyl fluoride and the like;

ethylenic unsaturated monoolefins such as propylene, butylene, isobutylene and the like.

Vinyl esters such as vinyl acetate, vinyl propionate, vinyl benzoate, vinyl butyrate and the like;

(metha)acrylates such as 2-ethylhexyl (metha)acrylate, stearyl(metha)acrylate, 2-chloroethyl(metha)acrylate, phenyl(metha)acrylate, α-chloro(metha)acrylate;

(metha)acrylic derivatives such as vinyl methyl ether, vinyl ethyl ether, vinyl isobutyl ether and the like;

vinyl ketones such as vinyl methyl ketone, vinyl hexyl ketone, methy isopropenyl ketone and the like;

N-vinyl compounds such as vinylpyrrole, N-vinylcarbazole, N-vinylindole, N-vinylpyrrolidone and the like; vinyl naphthalenes;

Monomers for polyamides are generally exemplified by dibasic acids such as terephthalic acid, isophthalic acid, adipic acid, maleic acid, succinic acid, sebacic acid, thioglycolic acid and the like; and diamines such as ethylene diamine, diaminoethyl ether, 1,4-diamino-benzene, 1,4-diaminobutane; caprolactam; and the like.

Monomers for urea resin are generally exemplified by diisocyanates such as p-phenylenediisocyanate, p-xylenediisocyanate, 1,4-tetramethylenediisocyanate and the like; and diamines such as ethylene diamines, diaminoethyl ether, 1,4-diaminobenzene, 1,4-diaminobutane and the like.

Monomers for epoxy resins are generally exemplified by amines such as ethyl amines, butyl amine, ethylenediamine, 1,4-diamiobenzene, 1,4-diaminobutane, monoethanol amine and the like; and diepoxides such as diglycidyl ether, ethylene glycol-diglycidyl ether, bisphenol A-diglycidyl ether, hydroquinone diglycidyl ether, and the like.

Monomers for polyesters are generally exemplified by polyols such ethylene glycol, diethylene glycol, triethylene glycol, 1,2-propylene glycol, 1,3-propylene glycol, 1,4-butanediol, 1,3-butanediol, 2,3-butanediol, 1,5-pentanediol, 1,6-hexanediol, neopentylglycol, 2-ethyl-1,3-hexanediol, 2,2,4-trimethyl-1,3-pentanediol, 1,4-bis(2-hydroxymethyl)cyclohexane, 2,2-bis(4-hydroxypropoxyphenyl)propane, bisphenol A, hydrogen-added bisphenol A, polyoxyethylene-treated bisphenol A and the like, and polybasic acids such maleic acid,fumaric acid, mesaconic acid, citraconic acid, itaconic acid, glutaconic acid, 1,2,4-benzene tricarboxylic acid, 1,2,5-benzene tricarboxylic acid, phthalic acid, terephthalic acid, isophthalic acid, succinic acid, adipic acid, malonic acid, sebacic acid, 1,2,4-cyclohexane tricarboxylic acid, 1,2,5-cyclohexane tricarboxylic acid, 1,2,4-butane tricarboxylic acid, 1,3-dicarboxy-2-methyl-2-methylcarboxypropane, tetra(methylcarboxy)methane, and esters of lower alcohols with anhydrides thereof, for example maleic anhydride, phthalic anhydride, tetrahydrophthalic acid anhydride, hexahydrophthalic acid anhydride, endomethylenetetrahydrophthalic anhydride, tetrachlorophthalic acid anhydride, tetrabromophthalic acid anhydride, dimethyl terephthalate and the like.

Polyesters may be prepared not only in combination of one kind of polyols with one kind of polybasic acid, but also in combination of two or more kinds of polyols with two or more kinds of polybasic acids. In particular, with respect to polybasic acids, unsaturated carboxylic acids are often combined with saturated carbooxylic acids, or polycarboxylic acids are often combined with polycarboxylic acid anhydrides.

Recently, a developing means which works at high speed is desired. A toner used in such a developing means at high speed is required to fix onto copying paper speedily and to separate from a fixing roller easily. From this view point, a resin constituting a toner such as homo and copolymer of styrenes, (metha)acrylic monomers and (metha)acrylate or polyesters have preferably a relationship between number average molecular weight (Mn), weight average molecular weight (Mw), and z average molecular weight (Mz) as below;

$$1000 \leq Mn \leq 7000$$

$$40 \leq Mw/Mn \leq 70$$

$$200 \leq Mz/Mn \leq 500$$

more preferably, Mn is $2000 \leq Mn \leq 7000$.

Polyester resins are excellent in resistance to polyvinylchloride, translucence required for transparent color toner and adhesion properties with OHP sheet.

When a polyester resin is applied to a transparent toner, it is preferable that the polyester resin is linear polymer and has 55°-70° C. in glass transition point, and 80°-150° C. in softening point. When a plyester resin is applied to a toner for an oilless fixing method, it is preferable that the polyester resin has 55°-80° C. in glass transition point, 80°-150° C. in softening point, and contains gel components at the content of 5-20 percents by weight. Such a polyester resin is negatively chargeable in nature, and so it is difficult to apply polyester resins to a positively chargeable toner. But, according to the present invention, a charge controlling agent of [I]-[III] can provide a polyester resin with practically sufficient positive chargeability.

Further a charge controlling agent of the present invention can be applied to a toner mainly constituted of a urethane-modified linear polyester. The urethane modified linear polyester in the present invention is the one prepared by reacting one mole of a linear polyester resin, which is formed by dicarboxylic acids and diols, and has average molecular weight of 1000-20000, acid value of 5 or less and hydroxy groups at the chain end, with 0.3-0.95 moles of diisocyanae, the modified linear polyester has 40°-80° C. in glass transition point and 5 or less in acid value.

A toner of the present invention may contain a little amount of positive-charge controlling agent other than a charge controlling agent of the present invention. Further, a very little amount of negative-charge controlling agent may be contained in order to stabilize chargeability. In those case, the total amount of charge controlling agents should be within the range as aforementioned.

A positive-charge controlling agent is exemplified by Nigrosine base EX (made by Orient Kagaku Kogyo K.K.), Quarternary Ammonium Salt P-51 (made by Orient Kagaku Kogyo K.K.) Nigrosine, Bontron N-01 (made by Orient Kagaku Kogyo K.K.) Sudan Schwaltz BB (Solvent Black 3; Color Index 26150), Fett Schwaltz HBN (C.I.No. 26150), Brilliant Spirit Schwaltz TN (made by Farbenfabriken Bayer AG), Zabon Schwaltz X (made by Farwerke Hoechst AG), alkoxylated amine, alkyl amide, molybdic acid chelate pigment or the like.

A negative charge-controlling agent is excemplified by Oil Black (color Index 26150), Oil Black BY (made by Orient Kagaku Kogyo K.K.), Bontron S-22 (made by Orient Kagaku Kogyo K.K.), Salicylic Acid Metal Complex E-81 (made by Orient Kagaku Kogyo K.K.), thioindigo pigments, sulfonyl amine derivatives of copper phthalocyanine, spilon Black TRH (made by Hodoya Kagaku Kogyo K.K.), Bontron S-34 (made by Orient Kagaku Kogyo K.K.), Nigrosine so (made by Orient Kagaku Kogyo K.K.), Seleschwaltz (R) G (made by Farbenfabriken Bayer AG) Chromogen Black ETOO (C.I. No. 14645), Azooil Black (R) (made by National Aniline) or the like.

Colorants contained in a toner for electrophotography are exemplified by various kinds of organic and inorganic pigments and dyes as follows; for a yellow pigment, is available chrome yellow, zinc yellow, cadmium yellow, yellow oxide, mineral fast yellow, nickel titanium yellow, nables yellow, naphthol yellow S, hansa yellow G, hansa yellow 10G, benzidine yellow G, benzidine yellow GR, quinoline yellow lake, permanent yellow, NCG, tartrazine lake or the like; for an orange pigment, is available chrome orange, molybdenum orange, permanent orange GTR, pyrazolone orange, vulcan orange, indanthrene brilliant orange RK, benzidine orange G, indanthrene brilliant orange GK or the like; for a red pigment, is available red iron oxide cadmium red, red lead oxide, cadmium mercury sulfide, permanent red 4R, lithol red, pyrazolone red, watchung red, calcium salt, lake red D, brilliant carmine 6B, eosine lake, rhodamine lake B, alizarin lake, brilliant carmine 3B or the like; for a purple pigment, is available manganese violet, fast violet B, methyl biolet lake or the like; for a blue pigment is available prussian blue cobalt blue, alkali blue lake victoria blue lake, phthalocyanine blue, metal-free phthalocyanine blue, phthalocyanine blue partial chlorine compound, fast sky blue, indanthrene blue BC or the like; for a green pigment, is available chrome green, chrome oxide green, pigment green B, mamachite green lake, fanal yellow green G or the like; and for a white pigment, is available zinc white titanium oxide, antimony white, zinc sulfide or the like.

For an extender pigment, is available powdery barytes, barium carbonate, clay, silica, white carbon talc, alumina white or the like.

- For black pigments, carbon black, cupric oxide, manganese dioxide, aniline black, activated carbon.

For various kinds of dyes such as basic dyes, acid dyes, disperse dyes, and direct dyes, nigrosine, methylene blue, rose bengale, quinoline yellow, ultramarine blue.

In use, one or more than two of them can be mixed. In any case, the limitation is not particularly given to the extender pigment, and other organic or inorganic pigments can be available, if they are pollution-free, and have high coloring power.

Such colorants can be used singly on in combination with other colorants at the content of 1-20 parts by weight, preferably 2-10 parts by weight on the basis of 100 parts by weight of toner-constituting resin. If the content is more than 20 parts by weight, fixing properties of toner may become poor. When it is less than 1 part by weight, sufficient image density may not be achieved.

Colorants, for transparent color toner are exemplified by various kinds of pigments and dyes as follows; for a yellow pigment, is available. C.I.10316 (naphthol yellow S), C.I.11710 (Hansa yellow 10 G), C.I.11660 (Hansa yellow 5G),C.I.11670 (Hansa yellow 3G), C.I.11680 (Hansa yellow G), C.I.11730 (Hansa yellow GR), C.I.11735 (Hansa yellow A), C.I.11740 (Hansa yellow RN), C.I.12710 (Hansa yellow R), C.I. 12720 (Hansa yellow L), C.I.21090 (benzidine yellow), C.I. 21095 (benzidine yellow G), C.I.21100 (benzidine yellow GR), C.I.20040 (permanent yellow NCG), C.I.21220 (vulcan fast yellow 5), C.I.21135 (vulcan fast yellow R) or the like.

For a red pigment, is available C.I.12055(sterling I), C.I.12075 (permanent orange), C.I.12175 (lithol fast orange 3GL), C.I.12305 (permanent orange GTR), C.I.11725 (hansa yellow 3R), C.I.21165 (vulcan fast orange GG), C.I.21110 (benzidine orange G), C.I.12120 (permanent red 4R) C.I. 1270 (para red), C.I.12085 (fire red), C.I.12315 (brilliant fast scarlet), C.I.12310 (permanent red F 2R), C.I.12335 (permanent red F4R), C.I.12440 (permanent red FRL), C.I.12460 (permanent red FRLL), C.I.12420 (permanent red F4RH), C.I.12450 (light fast red toner B), C.I.12490 (permanent carmine FB), C.I.15850 (brilliant carmine 6B) and the like.

For a blue pigment, is available C.I. 74100 (metal-free phthalocyanine blue), C.I.74160 (phthalocyanine blue), C.I.74180 (fast sky blue) or the like.

Such colorants can be used singly or in combination with other colorants at the content of 1–10 parts by weight, preferably 2–5 parts by weight on the basis of 100 parts by weight of toner-constituting resin. If the content is more than 10 parts by weight, fixing prpeties and transparent properties may become poor. When it is less than 1 part by weight, desired image density may not be achieved.

Off-set prevention agents may be incorporated into a toner to improve fixing properties. Off-set prevention agents are exemplifed by various kinds of wax, preferably polyolefin wax such as low molecular weight polypropylene, polyethylene, polypropylene of oxidized type and polyethylene of oxidized type. More preferable wax is the one that has 1000–20000 in number average molecular wight (Mn), 80°–150° C. in softening point (Tm). If the number average molecular weight Mn is less than 1000 or the softening point Tm is less than 80° C., the wax particles can not be dispersed uniformly in toner particles, resulting in the eluation of the wax to the surface of toner particles. The eluation of wax not only may have undesired influences on toner preservation and development but also may cause the pollution of photosensitive member by toner filming phenomenon If the number average molecular weight Mn is more than 20000 or the softenin pint Tm is more than 150° C., the compatibility of wax with resin becomes poor and the effects of wax, such as off-set resistance at high temperature or the like, can not be obtained. When a binder resin of toner contains plar groups, desirable wax is the one that also contains polar groups.

A toner of the present invention may be added with fluidization agents. Fluidization agents are exemplified by silica, aluminium oxide, titanium dioxide, a mixture of silica with aluminium oxide, a mixture of silica with titanium dioxide and the like.

A toner of the present invention can be applied to both a two-components developer and a single component developer (which may be magnetic or non-magnetic). When applied to a two components developer, a carrier may be the one per se known, for example, ferrite particles such as ferrite carrier, coated carrier, iron carrier with complex charging face.

A toner according to the present invention can be applied to development for electrostatic latent images used in electrophotography, electrorecording, electroprinting.

This invention is exemplified by examples. First, the synthetic method of a charging controlling agent represented by the general formula [XII].

Synthesis of a charge controlling agent [XII-1]

Thirteen hundred and forty five grams of styrene, 1353 g of dimethylaminoethyl-methacrylate, 1157 g of benzene and 13.5 g of azobisisobutyronitrile were mixed in a four-necked flask with a capacity of 5 liters, dissolved while stirring and reacted under a nitrogen stream at 80° C. for 8 hours for polymerization. Then, the temperature was increased to distill away benzene, the reminder was reduced to 50–70 mmHg at 180° C. to 190°60 C., and thereafter, the entire volitile content was removed. The resultant polymer was a crystal-clear solid, having a glass transition point of 55° C. and an amine value of 177.5 and referred to as charge controlling aent [XII-1].

Synthesis of a charge controlling agent [XII-2]

A charge controlling agent of general formula [XII] was synthesized in a manner similar to the synthesis of a charge controlling agent [XII-1] except that 2340 g of styrene, 392.5 g of dimethylaminoethylmethacrylate were used. The resultant polymer had a glass transition point of 76° C. and an amine value of 51, and referred to as a charge controlling agent [XII-2]

Synthesis of a charge controlling agent [XII-3]

Six hundred and twenty four grams of styrene, 632 g of dimethylaminoethyl-methacryalte, 1200 g of toluene and 5.4 g of azobisisobutyronitrile were mixed in a four-necked flask with a capacity of 3 liters, dissolved while stirring and reacted under a nitrogen stream at 80° C. for 6 hours for polymerization. Then, the temperature was increased to distill away toluene, the reminder was reduced to 40–50 mmHg at 180° C. to 190° C., and thereafter, the entire volitile content was removed. The resultant polymer was a crystal-clear solid, having a glass transition point of 56° C. and an amine value of 174 and referred to as charge controlling aent [XII-3].

EXAMPLE 1

Preparation of toners of A series

| ingredients | parts by weight |
| --- | --- |
| styrene-n-butyl methacrylate resin (softening point of 132° C. glass transition point of 60° C.) | 100 |
| carbon black (made by Mitsubishi Kasei K. K.) | 8 |
| Biscol 550 p (made by Sanyo Kasei Kogyo K. K.) | 5 |

The above-mentioned ingredients were sufficiently mixed in a ball mill, thereafter being kneaded over a three-roller heated to 140° C. The kneaded mixture was left to stand for cooling it, and coarsely pulverized in a feather mill. Then, the obtained particles were further pulverized into fine particles under jet stream, followed by being air-classified to obtain fine particles of 10 μm in mean particles size. Thus obtained particles are referred to as particle (i).

One hundred parts by weight of the obtained particle (i), and 0.3 parts by weight of a charge controlling agent shown in the column of Toner series of A in Tables 1–8 were set in Henschel mixer to agitate them at 1500 rpm for 2 minutes, so that the charge controlling agent might adhere to the surface of particle (i) electrostatically with the help of van der Waals forces.

The resultant particles were treated at 6000 rpm for 3 minuites in Hybridization System NHS-1 type (made by Nara Kikai Seisakusho K.K.) to fix the charge controlling agent on the surface of Particle (i).

Thus obtained toner is referred to as Toner A series.

EXAMPLE 2

Preparation of toners of B series

| ingredients | parts by weight |
| --- | --- |
| polyester resin Tafton NE-382: made by Kao K. K. | 100 |

-continued

| ingredients | parts by weight |
|---|---|
| brilliant (carmine 6B CI 15850) | 3 |
| a charge controlling agent shown in the column of Toner series of B in Tables 1-8 | 4 |

The above mentioned ingredients were sufficiently mixed in a ball mill, thereafter being kneaded over a three-roller heated to 140° C. The kneaded mixture was left to stand for cooling it, and coarsely pulverized in a feather mill. Then, the obtained particles were further plverized into fine particles under jet stream, followed by being air-classified to obtain fine particles of 11 μm in mean particle size. Thus obtained particles are referred to as Toner B series.

EXAMPLE 3

Preparation of toners of C series

| ingredients | parts by weight |
|---|---|
| polyester resin (NE-1110; made by Kao) | 100 |
| carbon black (MA#8; made by Mitsubishi Kasei Kogo K. K.) | 8 |
| low molecular weight polypropylene of oxidized type (Biscol TS-200; made by Sanyo Kasei Kogyo K. K.) | 3 |
| a charge controlling agent shown in the column of Toner series of C in Tables 1-8 | 5 |

Fine particles of 11 μm in means paricle size were prepared in a manner similar to preparation of toners of B series using above mentioned ingredients.

Thus obtained particles were referred to as Toner C series.

EXAMPLE 4

Preparation of toners of D series

| ingredients | parts by weight |
|---|---|
| polyester resin (NE-382; made by Kao K. K.) | 100 |
| phthalocyanine pigment | 3 |

Fine particles containing a colorant were prepared in a manner similar to preparation of toners of A series using ingredients above mentioned.

One hundred parts by weight of the obtained particles, and 0.3 parts by weight of a charge controlling agent shown in the column of Toner series of D in Tables 1-8 were set in Henschel mixer to agitate them at 1500 rpm for 2 minutes, so that the charge controlling agent might adhere to the surface of the particles electrostatically with the help of van der Waals forces.

The resultant particles were treated at 6000 rpm for 3 minuites in Hybridization System NHS-1 type (made by Nara Kikai Seisakusho K.K.) to fix the charge controlling agent on the surface of the particles.

Thus obtained toner is referred to as Toner D series.

Example 5

Preparation of toners of E series

One hundred parts by weight of spherical copolymer particles in mono-dispersion of styrene with n-butylmethacrylate prepared by seed-polymerization (6 μm in mean particle size; 54° C. in softening point; 128° C. in softening point; 15% in gel components content (insoluble in toluene)), 8 parts by weight of carbon black (MA#8; made by Mitsubishi Kasei Kogyo) were set in Henschel mixer with a capacity of 10 liters for agitation at 1500 rpm for 2 minutes to adhere carbon black to the surface of the polymer particles. The obtained polyer particles were treated at 6000 rpm for 3 minutes in Hybridization System NHS-1 type (made by Nara Kikai Seisakusho K.K.) to fix the carbon black particles on the surface of the polymer particles.

Then, the resultant polymer particles of 100 parts by weight were treated with MMA/iBMA (1:9) particles (MP-4951; 0.2 μm in mean particle size; 85° C. in glass transition point; made by Soken Kagaku K.K.;) in Hybridization System in a manner as above except for revolution number of 8000 rpm and treatment time of 5 minutes to coat the polymer particles with resin. Thus obtained particles of 100 parts by weight were further treated with a charge controlling agent shown in the column of toner series of E in tables 1-8 of 0.5 parts by weight in Hybridization system in a manner similar to that of the formation of carbon-black layer as above mentioned to fix the particles of the charge controlling agent on the polymer particles. Thus, obtained particles had mean partcle size of 6.5 μm, spheroidicity of 132 and coefficient of variation of 18%, being referred to as Toner E series.

COMPARATIVE EXAMPLE 1

Fine particles of 11 μm in mean particle size were prepared in a manner similar to Example 3 except that Bontron N-01 (nigrosine series;.made by Orient Kagaku Kogyo K.K.) of 5 parts by weight as a charge controlling agent.

The obtained particles are referred to as Toner F.

COMPARATIVE EXAMPLE 2

Fine particles of 11 μm in mean particle size were prepared in a manner similar to Example 3 except that 2-aminobenzimidazole of 5 parts by weight was used as a charge controlling agent.

The obtained particles are referred to as Toner G.

EXAMPLE 6

Preparation of toners of H series

Fine particles of 11 μm were prepared in a manner similar to Example 2 except that the ingredients below were used;

| ingredient | parts by weight |
|---|---|
| thermoplastic styrene-acrylic resin Mn: 4200  Mw: 213400 Mz: 1323000  Mw/Mn: 50.2 Mz:Mn: 315  acid value: 25.8 softening point: 115° C. Tg: 62° C. | 100 |
| carbon black (made by Mitsubishi Kasei Kogyo K. K.) | 8 |
| low molecular weight polypropylene (Biscol 605 p; made by Sanyo Kasei Kogyo K. K.) | 4 |
| a charge controlling agent shown | 3 |

-continued

| ingredient | parts by weight |
|---|---|
| in the column of Toner series of H in Tables 1-8 | |

The obtained particles are referred to as Toner H series.

EXAMPLE 7

Preparation of toners of I series

Fine particles of 11 μm were prepared in a manner similar to Example 2 except that the ingredients below were used;

| ingredient | parts by weight |
|---|---|
| thermoplastic polyester resin | 100 |
| Mn: 3400   Mw: 213400 | |
| Mz: 1183200   Mw/Mn: 62.8 | |
| Mz:Mn: 348   acid value: 16.7 | |
| softening point: 109° C. Tg: 64° C. | |
| lake red C (made by Dainichi Seika Kogyo K. K.) | 5 |
| low molecular weight polypropylene of oxidized type (Biscol TS-200; made by Sanyo Kasei Kogyo K. K.) | 5 |
| a charge controlling agent shown in the column of Toner series of I in Tables 1-8 | 3 |

The obtained particles are referred to as Toner I series.

EXAMPLE 8

Preparation of toners of J series

Fine particles of 11 μm were prepared in a manner similar to Example 2 except that the ingredients below were used;

| ingredients | parts by weight |
|---|---|
| urethan modified linear polyester resin | 100 |
| Mn: 4000   Mw: 35400 | |
| Mw/Mn: 8.9   Tg: 56° C. | |
| acid value: 0.8 | |
| copper phthalocyanine (made by dainichi Seika Kogyo K.K.) | 5 |
| low molecular weight polypropylene (Biscol 605P; made by Sanyo Kasei Kogyo K.K.) | 4 |
| a charge controlling agent shown in the column of Toner series of J in Table 1-8 | 3 |

COMPARATIVE EXAMPLE 3

Preparation of toner K

Fine particles of 11 μm in mean particle size were prepared in a manner similar to Example 7 except that Nigrosine base EX (made by Orient Kagaku Kogyo K.K.)

The obtained particles are referred to as Toner K.

COMPARATIVE EXAMPLE 4

Preparation of toner L

Fine particles of 11 μm in means particle size were prepared in a manner similar to Example 8 except that quarternary ammonium salt p-51 (made by Orient Kagaku Kogyo K.K.) was used as a charge controlling agent.

Thus obtained particles are referred to as Toner L.
Thus obtained particles are referred to as Toner J series.

EXAMPLE 9

Preparation of toners of M series

Fine particles of 10.2 μm in means particle size were prepared in a manner similar to the preparation of Particle (i) except that the ingredients below were used;

| ingredient | parts by weight |
|---|---|
| polyester resin | 100 |
| Mn: 3400   Mw: 213400 | |
| Mz: 1183200   Mw/Mn: 62.8 | |
| Mz/Mn: 348   acid value: 16.7 | |
| softening point: 109° C.   Tg: 64° C. | |
| low molecular weight polypropylene of oxidized type (pyrolysis product of polypropylene; viscosity at 160° C.: 140 cps; acid value 5) | 5 |
| carbon black MA #8 (made by Mitsubishi Kasei Kogyo K.K.) | 8 |

One hundred parts by weight of the above obtained particle, and 0.3 parts by weight of a charge controlling agent shown in the column of Toner series of M in Tables 1-8 were set in Henschel mixer to agitate them at 1500 rpm for 2 minutes, so that the charge controlling agent might adhere to the surface of the particles electrostatically with the help of van der Waals forces.

The resultant particles were treated at 6000 rpm for 3 minuites in Hybridization System NHS-1 type (made by Nara Kikai Seisakusho K.K.) to fix the charge controlling agent on the surface of the particles.

Thus obtained toner is referred to as Toner M series.

COMPARATIVE EXAMPLE 5

Preparation of toner

Toner N of 10.3 μm in mean particle size was prepared in a manner similar to Example 9 except that Bontron N-01 of nigrosine series (made by Orient Kagaku Kogyo K.K.) was used as a charge controlling agent.

EXAMPLE 10

Preparation of toners of O series

One hundred parts by weight of colorant-containing resin particles of 8 μm in mean particle size prepared in a manner similar to Example 4, 15 parts by weight of MMA/iBMA (1:9) particles (MP-4951; 0.2 μm in mean particle size; 85° C. in glass transition point; made by Soken Kagaku K.K.), and 1 part by weight of a charge controlling agent shown in the column of Toner series of O were put into O.M. dizer (made by Nara Kikai Seisakusho K.K.) for agitation at 1200 rpm for 2 minutes. Then, the obtained mixture was further treated in Hybridization system (NHS-1 type; made by Nara Kikai Seisakusho K.K.) at 8000 rpm for 5 minutes to form resin layers containing the charge controlling agent around the resin particles.

The resultant particles are referred to as Toner O series.

EXAMPLE 11

Preparation of toners of P series

Toners of P series were prepared in a manner similar to Example 6 except that thermoplastic resin having

| | |
|---|---|
| Mn: 12800 | Mw: 178900 |
| Mz: 957600 | Mw/Mn: 14.0 |
| Mz/Mn: 75 | Tg: 62.3° C. |
| softening point: 127° C. was used. | | the obtained toners were 10.8 μm in mean particle size respectively.

EXAMPLE 12

Toners of Q series were prepared in a manner similar to Example 6 except that thermoplastic resin having

| | |
|---|---|
| Mn: 4800 | Mw: 374400 |
| Mz: 3321600 | Mw/Mn: 78 |
| Mz/Mn: 692 | Tg: 66.2 | was used.

The obtained toners were 11.2 μm in mean particle size respectively.

Preparation of Carrier

A binder type carrier was prepared as below to evaluate the above obtained toners.

| ingredients | parts by weight |
|---|---|
| polyester resin (NE-1110; made by Kao K.K.) | 100 |
| inorganic magnetic particles (EPT-1000; made by Toda Kogyo K.K.) | 500 |
| carbon black (MA #8; Mitsubishi Kasei K.K.) | 2 |

The above ingredients were mixed sufficiently in a Henschel mixer, pulverized and fused and kneaded using an extrusion kneader wherein the temperature of cylinder and cylinder head was set at 180° C. and 170° C., respectively. The kneaded mixture was cooled, then pulverized in a jet mill, then classified using a classifier to obtain magnetic carrier of an average particle diameter of 55 μm.

Particle size measurement (1) Particle size of carrier

The particle size of the carrier was measured with Micro track model 7995-10 SRA (made by Nikkiso K.K.) to obtain mean particle size.

(2) Particle size of toners

The mean particle size of toner particles were obtained by measuring relative weight distribution of particle size with aperture tube of 100 μm.

Evaluation of various kinds of properties

Each of Toners above obtained of 100 parts by weight was surface-treated with Colloidal silica R-972 (made by Nippon Aerosil) of 0.1 part by weight to be subjected to evaluation tests below;

(1) Measurement of charge Amount (Q/M) and Flying Amount

Each five grams of the surface-treated toner and 28 g of carrier were put in a poly bottle of a capacity of 50 cc, and were stirred at 1200 rpm for 10 minutes to evluate electrification build up properties, charge amount of toner and toner flying amount at the same time. The charge amount of toner and the toner flying amount were also measured after a poly bottle containing toner and carrier at the same ratio as above was preserved under conditions of 35° C. of temperature and 85 % of relative humidity.

The flying amount was measured with the use of a digital dust measuring apparatus of P5H2 type (manufactured by Shibata Kagakusha K.K.). The dust measuring apparatus was spaced 10 cm apart from a magnet roll, and 2 g of the developer was set on the magnet roll, which was rotated at 2,000 rpm. Then, the dust measuring apparatus detected the toner particles flying about as dust, and displayed the resultant value in the number of counts per minute, i.e. cpm.

The results were shown in Tables 1–8. In the tables 1–8, the symbol "o" represents the toner flying amount of 300 cpm or less, the symbol "Δ" represents the toner flying amount of 500 cpm or less, and the symbol "x" represents the toner flying amount of 500 cpm or more. When the rank is higher than "Δ", the toner can be used practically. The preferable rank is "o".

Properties with respect to copy

Each of toners obtained above was mixed with the carrier at the 7/93 ratio (toner to carrier) to prepare a two components developer. Developers containing toners of Examples 1–12 and comparative examples 1–5 were provided for EP-470z (system speed of 18 cm/sec; made by Minolta Camera) to evaluate various kinds of properties with respect to copy. But, developers containing toners of Examples 2, 4 and 10 were provided for EP-470z equipped with a fixing machine of an oil-spread type.

(1) fogs with respect to copy

Each of developers as above obtained was used in the formation of copied images to observe fogs on the copy ground. The degree of fogs was ranked with the symbols "o" and "Δ". The results were shown in Tables 1–8. When the rank is higher than "Δ", the toner can be put into practical use. The preferable rank is "o".

(2) durability with respect to copy

Each of developers as above obtained was subjected to durability test with respect to 100000 times of copy of the chart with the B/W ratio of 6 %. The results were shown in Tables 1–8. The symbol "o" in the table means that there is no problem with respect to practical use and "x" means there are some problems with respect ot practical use.

(3) translucence

Toners obtained in Examples of 2, 4 and 10 were subjected to a translucence test. The translucence was observed on the clearity of color with the naked eyes when copied images fixed on OHP sheet were projected by a OHP projector. The results were shown in tables 1–8. The symbol "o" in the Tables means that the toner can be put into practical use with respect to color-reproducibility.

Humid resistant test

After EP-470Z copying machine was left under high hummid conditions of 35° C., and 85 % in relative humidity for 24 hours, copied images, charging amounts and toner flying amount were evaluated.

fixing properties at high speed

Developers constituted of toners obtained in Examples 6, 7, 9, 11 and 12 were evaluated with respect to fixing properties at high speed.

The generation of off-set at high temperature, the generation of off-set at low temperature and the fixing strength of ID1.2 and I.D.0.6 at 175° C. in fixing temperature were measured by fixing a toner through between a fixing roller (60 Φ) coated with resin of teflon series and a LTV rubber roller, which was compressed against the fixing roller at the pressure of 10 Kg, and passing therebetween at the revolution speed of 45 cm/sec.

The off-set at high temperature means the phenomenon that toner particles adhereing to a heat roller because of fusion or softening of the particles are transferred onto a copying paper at the second contact with a copying paper. The off-set at low temperature means the phenomena that toner particles adhering not to copying paper but to a heat roller because of uncompletely fusion are transferred onto a copying paper at the second contact with a copying paper.

I.D. means image density measured by Sakura reflecting densitometer.

I.D. requires 80 % or more in ID1.2 and 70% or more in ID0.6.

Non off-set width requires 100° C. or more.

The fixing strength is the ratio of reflection temperature of copied images before and after the copied images are erased with a sand eraser of special make at the pressure of 1 kg.

The evolutions are summed up by the symbols "o" and "x", wherein "o" means that it can be practically used and "x" means that it can not be used.

Heat resistance

Fifty grams of toner were put into a glass sample bottle (50 cc) and left to stand in an oven set at 50° C. ±0.5° C. for 24 hours. Thereafter, the sample bottle was taken out from the oven and cooled to room temperature. Then, the bottle was stood reversely to observe whether the toner fell.

A: fell during 0–5 seconds; no aggregation
B: fell during 5–15 seconds; no aggregation
C: fell during 15–30 seconds; a slight aggregation (the aggregation is broken when shaken fully)
D: fell during 30–60 seconds; a weak aggregation (the aggregation is not broken in spite of enough shake).
E: not fell even after 60 seconds; the toner aggregated as solids at the bottom of the bottle.

TABLE 1

| | Toner Series | charge controlling agent No. | evaluation of initial stage | | | evaluation of humid resistance | | | evaluation of durability with respect to copy (copied images/fogs) | | | | |
|---|---|---|---|---|---|---|---|---|---|---|---|---|---|
| | | | Q/M (μC/g) | toner flying | copied images/ fogs | Q/M (μC/g) | toner flying | copied images/ fogs | 1000 | 5000 | 10000 | 50000 | 100000 |
| | | | | | | | | | | | (sheets) | | |
| Example | A | I-3 | +15 | O | O | +15 | O | O | O | O | O | O | O |
| Example | B | I-4 | +13 | O | O | +13 | O | O | O | O | O | O | O |
| Example | C | I-26 | +12 | O | O | +12 | O | O | O | O | O | O | O |
| Example | D | I-10 | +16 | O | O | +15 | O | O | O | O | O | O | O |
| Example | E | I-1 | +19 | O | O | +18 | O | O | O | O | O | O | O |
| Comparative Example | F | Bontron N-01; one of Nigrosines | +7 | Δ | Δ | +4 | X | X | X | — | — | — | — |
| Comparative Example | G | 2-amino-benzaldehyde | +10 | Δ | Δ | +4 | X | X | Δ | Δ | X | — | — |
| Example | H | I-3 | +15 | O | O | +15 | O | O | O | O | O | O | O |
| Example | I | I-4 | +13 | O | O | +12 | O | O | O | O | O | O | O |
| Example | J | I-4 | +15 | O | O | +15 | O | O | O | O | O | O | O |
| Comparative Example | K | Nigrosine base EX | +9 | Δ | Δ | +6 | X | X | X | — | — | — | — |
| Comparative Example | L | quarternary ammonium salt | +5 | X | X | +3 | X | X | — | — | — | — | — |
| Example | M | I-18 | +14 | O | O | +14 | O | O | O | O | O | O | O |
| Comparative Example | N | Bontron N-01; one of Nigrosines | +10 | X | Δ | +7 | X | X | X | — | — | — | — |
| Example | O | I-9 | +14 | O | O | +13 | O | O | O | O | O | O | O |
| Example | P | I-3 | +13 | O | O | +11 | O | O | O | O | O | O | O |
| Example | Q | I-3 | +12 | O | O | +10 | O | O | O | O | O | O | O |

| | Toner Series | translucence | fixing properties at high speed development | remarks |
|---|---|---|---|---|
| Example | A | — | — | |
| Example | B | O | — | oil spread fixing |
| Example | C | — | — | |
| Example | D | O | — | oil spread fixing |
| Example | E | — | — | |
| Comparative Example | F | — | — | stopped durability test after 1000 times copy because of much fogs |
| Comparative Example | G | — | — | stopped durability test after 1000 times copy because of much fogs |
| Example | H | — | O | |
| Example | I | — | O | |
| Example | J | — | | |
| Comparative Example | K | — | — | stopped durability test after 1000 times copy because of much fogs |
| Comparative Example | L | — | — | could not carry out durability-test because of much fogs at initial |

TABLE 1-continued

| | | | | | |
|---|---|---|---|---|---|
| Example | M | — | ○ | | stage of copy |
| Comparative Example | N | — | — | | stopped durability test after 1000 times copy because of much fogs and missing images |
| Example | O | ○ | — | | oil spread fixing |
| Example | P | — | X | | |
| Example | Q | — | X | | |

TABLE 2

| | Toner Series | charge controlling agent No. | evaluation of initial stage | | | evaluation of humid resistance | | | evaluation of durability with respect to copy (copied images/fogs) | | | | |
|---|---|---|---|---|---|---|---|---|---|---|---|---|---|
| | | | Q/M (μC/g) | toner flying | copied images/ fogs | Q/M (μC/g) | toner flying | copied images/ fogs | 1000 | 5000 | 10000 (sheets) | 50000 | 100000 |
| Example | A | II-3 | +13 | ○ | ○ | +13 | ○ | ○ | ○ | ○ | ○ | ○ | ○ |
| Example | B | II-4 | +15 | ○ | ○ | +15 | ○ | ○ | ○ | ○ | ○ | ○ | ○ |
| Example | C | II-9 | +16 | ○ | ○ | +16 | ○ | ○ | ○ | ○ | ○ | ○ | ○ |
| Example | D | II-10 | +14 | ○ | ○ | +14 | ○ | ○ | ○ | ○ | ○ | ○ | ○ |
| Example | E | II-11 | +18 | ○ | ○ | +18 | ○ | ○ | ○ | ○ | ○ | ○ | ○ |
| Example | H | II-3 | +15 | ○ | ○ | +15 | ○ | ○ | ○ | ○ | ○ | ○ | ○ |
| Example | I | II-4 | +13 | ○ | ○ | +12 | ○ | ○ | ○ | ○ | ○ | ○ | ○ |
| Example | J | II-4 | +15 | ○ | ○ | +15 | ○ | ○ | ○ | ○ | ○ | ○ | ○ |
| Example | M | II-4 | +14 | ○ | ○ | +14 | ○ | ○ | ○ | ○ | ○ | ○ | ○ |
| Example | O | II-16 | +13 | ○ | ○ | +13 | ○ | ○ | ○ | ○ | ○ | ○ | ○ |
| Example | P | II-3 | +12 | ○ | ○ | +12 | ○ | ○ | ○ | ○ | ○ | ○ | ○ |
| Example | Q | II-3 | +14 | ○ | ○ | +14 | ○ | ○ | ○ | ○ | ○ | ○ | ○ |

| | Toner Series | translucence | fixing properties at high speed development | remarks |
|---|---|---|---|---|
| Example | A | — | — | |
| Example | B | ○ | — | oil spread fixing |
| Example | C | — | — | |
| Example | D | ○ | — | oil spread fixing |
| Example | E | — | — | |
| Example | H | — | ○ | |
| Example | I | — | ○ | |
| Example | J | — | — | |
| Example | M | — | ○ | |
| Example | O | ○ | — | oil spread fixing |
| Example | P | — | X | |
| Example | Q | — | X | |

TABLE 3

| | Toner Series | charge controlling agent No. | evaluation of initial stage | | | evaluation of humid resistance | | | evaluation of durability with respect to copy (copied images/fogs) | | | | |
|---|---|---|---|---|---|---|---|---|---|---|---|---|---|
| | | | Q/M (μC/g) | toner flying | copied images/ fogs | Q/M (μC/g) | toner flying | copied images/ fogs | 1000 | 5000 | 10000 (sheets) | 50000 | 100000 |
| Example | A | VII-1 | +13 | ○ | ○ | +13 | ○ | ○ | ○ | ○ | ○ | ○ | ○ |
| Example | B | VII-2 | +12 | ○ | ○ | +12 | ○ | ○ | ○ | ○ | ○ | ○ | ○ |
| Example | C | VII-6 | +11 | ○ | ○ | +10 | ○ | ○ | ○ | ○ | ○ | ○ | ○ |
| Example | D | VII-13 | +14 | ○ | ○ | +13 | ○ | ○ | ○ | ○ | ○ | ○ | ○ |
| Example | E | VII-15 | +18 | ○ | ○ | +18 | ○ | ○ | ○ | ○ | ○ | ○ | ○ |
| Example | H | VII-1 | +15 | ○ | ○ | +14 | ○ | ○ | ○ | ○ | ○ | ○ | ○ |
| Example | I | VII-2 | +12 | ○ | ○ | +12 | ○ | ○ | ○ | ○ | ○ | ○ | ○ |
| Example | J | VII-2 | +14 | ○ | ○ | +14 | ○ | ○ | ○ | ○ | ○ | ○ | ○ |
| Example | M | VII-7 | +13 | ○ | ○ | +12 | ○ | ○ | ○ | ○ | ○ | ○ | ○ |
| Example | O | VII-2 | +13 | ○ | ○ | +12 | ○ | ○ | ○ | ○ | ○ | ○ | ○ |
| Example | P | VII-1 | +12 | ○ | ○ | +12 | ○ | ○ | ○ | ○ | ○ | ○ | ○ |
| Example | Q | VII-1 | +14 | ○ | ○ | +13 | ○ | ○ | ○ | ○ | ○ | ○ | ○ |

| | Toner Series | translucence | fixing properties at high speed development | remarks |
|---|---|---|---|---|
| Example | A | — | — | |
| Example | B | ○ | — | oil spread fixing |
| Example | C | — | — | |
| Example | D | ○ | — | oil spread fixing |
| Example | E | — | — | |
| Example | H | — | ○ | |
| Example | I | — | ○ | |
| Example | J | — | — | |
| Example | M | — | ○ | |
| Example | O | ○ | — | oil spread fixing |
| Example | P | — | X | |

TABLE 3-continued

| | Example | Q | — | X |
|---|---|---|---|---|

TABLE 4

| | Toner Series | charge controlling agent No. | evaluation of initial stage | | | evaluation of humid resistance | | |
|---|---|---|---|---|---|---|---|---|
| | | | Q/M (μC/g) | toner flying | copied images/ fogs | Q/M (μC/g) | toner flying | copied images/ fogs |
| Example | A | VIII-3 | +14 | ○ | ○ | +14 | ○ | ○ |
| Example | B | VIII-4 | +14 | ○ | ○ | +14 | ○ | ○ |
| Example | C | VIII-10 | +13 | ○ | ○ | +13 | ○ | ○ |
| Example | D | VIII-9 | +16 | ○ | ○ | +16 | ○ | ○ |
| Example | E | VIII-4 | +20 | ○ | ○ | +19 | ○ | ○ |
| Example | H | VIII-3 | +16 | ○ | ○ | +16 | ○ | ○ |
| Example | I | VIII-4 | +14 | ○ | ○ | +13 | ○ | ○ |
| Example | J | VIII-4 | +16 | ○ | ○ | +15 | ○ | ○ |
| Example | M | VIII-10 | +13 | ○ | ○ | +13 | ○ | ○ |
| Example | O | VIII-15 | +13 | ○ | ○ | +13 | ○ | ○ |
| Example | P | VIII-3 | +12 | ○ | ○ | +12 | ○ | ○ |
| Example | Q | VIII-3 | +12 | ○ | ○ | +11 | ○ | ○ |

| | Toner Series | evaluation of durability with respect to copy (copied images/fogs) | | | | | trans- lu- cence | fixing properties at high speed development | remarks |
|---|---|---|---|---|---|---|---|---|---|
| | | 1000 (sheets) | 5000 | 10000 | 50000 | 100000 | | | |
| Example | A | ○ | ○ | ○ | ○ | ○ | — | — | |
| Example | B | ○ | ○ | ○ | ○ | ○ | ○ | — | oil spread fixing |
| Example | C | ○ | ○ | ○ | ○ | ○ | — | — | |
| Example | D | ○ | ○ | ○ | ○ | ○ | ○ | — | oil spread fixing |
| Example | E | ○ | ○ | ○ | ○ | ○ | — | — | |
| Example | H | ○ | ○ | ○ | ○ | ○ | — | ○ | |
| Example | I | ○ | ○ | ○ | ○ | ○ | — | ○ | |
| Example | J | ○ | ○ | ○ | ○ | ○ | — | — | |
| Example | M | ○ | ○ | ○ | ○ | ○ | — | ○ | |
| Example | O | ○ | ○ | ○ | ○ | ○ | ○ | — | oil spread fixing |
| Example | P | ○ | ○ | ○ | ○ | ○ | — | × | |
| Example | Q | ○ | ○ | ○ | ○ | ○ | — | × | |

TABLE 5

| | Toner Series | charge controlling agent No. | evaluation of initial stage | | | evaluation of humid resistance | | |
|---|---|---|---|---|---|---|---|---|
| | | | Q/M (μC/g) | toner flying | copied images/ fogs | Q/M (μC/g) | toner flying | copied images/ fogs |
| Example | A | IX-2 | +15 | ○ | ○ | +15 | ○ | ○ |
| Example | B | IX-4 | +15 | ○ | ○ | +15 | ○ | ○ |
| Example | C | IX-7 | +13 | ○ | ○ | +12 | ○ | ○ |
| Example | D | IX-9 | +15 | ○ | ○ | +15 | ○ | ○ |
| Example | E | IX-14 | +17 | ○ | ○ | +17 | ○ | ○ |
| Example | H | IX-7 | +15 | ○ | ○ | +15 | ○ | ○ |
| Example | I | IX-4 | +14 | ○ | ○ | +13 | ○ | ○ |
| Example | J | IX-4 | +16 | ○ | ○ | +16 | ○ | ○ |
| Example | M | IX-8 | +14 | ○ | ○ | +14 | ○ | ○ |
| Example | O | IX-10 | +13 | ○ | ○ | +13 | ○ | ○ |
| Example | P | IX-7 | +13 | ○ | ○ | +13 | ○ | ○ |
| Example | Q | IX-7 | +14 | ○ | ○ | +14 | ○ | ○ |

| | Toner Series | evaluation of durability with respect to copy (copied images/fogs) | | | | | trans- lu- cence | fixing properties at high speed development | remarks |
|---|---|---|---|---|---|---|---|---|---|
| | | 1000 (sheets) | 5000 | 10000 | 50000 | 100000 | | | |
| Example | A | ○ | ○ | ○ | ○ | ○ | — | — | |
| Example | B | ○ | ○ | ○ | ○ | ○ | ○ | — | oil spread fixing |
| Example | C | ○ | ○ | ○ | ○ | ○ | — | — | |
| Example | D | ○ | ○ | ○ | ○ | ○ | ○ | — | oil spread fixing |
| Example | E | ○ | ○ | ○ | ○ | ○ | — | — | |
| Example | H | ○ | ○ | ○ | ○ | ○ | — | ○ | |
| Example | I | ○ | ○ | ○ | ○ | ○ | — | ○ | |
| Example | J | ○ | ○ | ○ | ○ | ○ | — | — | |
| Example | M | ○ | ○ | ○ | ○ | ○ | — | ○ | |
| Example | O | ○ | ○ | ○ | ○ | ○ | ○ | — | oil spread fixing |
| Example | P | ○ | ○ | ○ | ○ | ○ | — | × | |
| Example | Q | ○ | ○ | ○ | ○ | ○ | — | × | |

TABLE 6

| | Toner Series | charge controlling agent No. | evaluation of initial stage | | | evaluation of humid resistance | | |
|---|---|---|---|---|---|---|---|---|
| | | | Q/M (μC/g) | toner flying | copied images/ fogs | Q/M (μC/g) | toner flying | copied images/ fogs |
| Example | A | X-4 | +16 | ○ | ○ | +15 | ○ | ○ |
| Example | B | X-5 | +15 | ○ | ○ | +15 | ○ | ○ |
| Example | C | X-11 | +13 | ○ | ○ | +13 | ○ | ○ |
| Example | D | X-13 | +17 | ○ | ○ | +16 | ○ | ○ |
| Example | E | X-1 | +16 | ○ | ○ | +16 | ○ | ○ |
| Example | H | X-8 | +13 | ○ | ○ | +13 | ○ | ○ |
| Example | I | X-9 | +13 | ○ | ○ | +12 | ○ | ○ |
| Example | J | X-14 | +16 | ○ | ○ | +15 | ○ | ○ |
| Example | M | X-18 | +16 | ○ | ○ | +16 | ○ | ○ |
| Example | O | X-25 | +16 | ○ | ○ | +15 | ○ | ○ |
| Example | P | X-8 | +14 | ○ | ○ | +12 | ○ | ○ |
| Example | Q | X-8 | +13 | ○ | ○ | +11 | ○ | ○ |

| | Toner Series | evaluation of durability with respect to copy (copied images/fogs) | | | | | trans- lu- cence | fixing properties at high speed development | remarks |
|---|---|---|---|---|---|---|---|---|---|
| | | 1000 (sheets) | 5000 | 10000 | 50000 | 100000 | | | |
| Example | A | ○ | ○ | ○ | ○ | ○ | — | — | |
| Example | B | ○ | ○ | ○ | ○ | ○ | ○ | — | oil spread fixing |
| Example | C | ○ | ○ | ○ | ○ | ○ | — | — | |
| Example | D | ○ | ○ | ○ | ○ | ○ | ○ | — | oil spread fixing |
| Example | E | ○ | ○ | ○ | ○ | ○ | — | — | |
| Example | H | ○ | ○ | ○ | ○ | ○ | — | ○ | |
| Example | I | ○ | ○ | ○ | ○ | ○ | — | ○ | |
| Example | J | ○ | ○ | ○ | ○ | ○ | — | — | |
| Example | M | ○ | ○ | ○ | ○ | ○ | — | ○ | |
| Example | O | ○ | ○ | ○ | ○ | ○ | ○ | — | oil spread fixing |
| Example | P | ○ | ○ | ○ | ○ | ○ | — | × | |
| Example | Q | ○ | ○ | ○ | ○ | ○ | — | × | |

TABLE 7

| | Toner Series | charge controlling agent No. | evaluation of initial stage | | | evaluation of humid resistance | | |
|---|---|---|---|---|---|---|---|---|
| | | | Q/M (μC/g) | toner flying | copied images/ fogs | Q/M (μC/g) | toner flying | copied images/ fogs |
| Example | A | XI-4 | +18 | ○ | ○ | +18 | ○ | ○ |
| Example | B | XI-5 | +15 | ○ | ○ | +15 | ○ | ○ |
| Example | C | XI-9 | +13 | ○ | ○ | +13 | ○ | ○ |
| Example | D | XI-10 | +18 | ○ | ○ | +17 | ○ | ○ |
| Example | E | XI-14 | +20 | ○ | ○ | +20 | ○ | ○ |
| Example | H | XI-24 | +16 | ○ | ○ | +16 | ○ | ○ |
| Example | I | XI-26 | +14 | ○ | ○ | +14 | ○ | ○ |
| Example | J | XI-26 | +17 | ○ | ○ | +17 | ○ | ○ |
| Example | M | XI-29 | +16 | ○ | ○ | +16 | ○ | ○ |
| Example | O | XI-9 | +15 | ○ | ○ | +14 | ○ | ○ |
| Example | P | XI-24 | +14 | ○ | ○ | +12 | ○ | ○ |
| Example | Q | XI-24 | +13 | ○ | ○ | +12 | ○ | ○ |

| | Toner Series | evaluation of durability with respect to copy (copied images/fogs) | | | | | trans- lu- cence | fixing properties at high speed development | remarks |
|---|---|---|---|---|---|---|---|---|---|
| | | 1000 (sheets) | 5000 | 10000 | 50000 | 100000 | | | |
| Example | A | ○ | ○ | ○ | ○ | ○ | — | — | |
| Example | B | ○ | ○ | ○ | ○ | ○ | ○ | — | oil spread fixing |
| Example | C | ○ | ○ | ○ | ○ | ○ | — | — | |
| Example | D | ○ | ○ | ○ | ○ | ○ | ○ | — | oil spread fixing |
| Example | E | ○ | ○ | ○ | ○ | ○ | — | — | |
| Example | H | ○ | ○ | ○ | ○ | ○ | — | ○ | |
| Example | I | ○ | ○ | ○ | ○ | ○ | — | ○ | |
| Example | J | ○ | ○ | ○ | ○ | ○ | — | — | |
| Example | M | ○ | ○ | ○ | ○ | ○ | — | ○ | |
| Example | O | ○ | ○ | ○ | ○ | ○ | ○ | — | oil spread fixing |
| Example | P | ○ | ○ | ○ | ○ | ○ | — | × | |
| Example | Q | ○ | ○ | ○ | ○ | ○ | — | × | |

TABLE 8

| Toner | parts by | charge controlling | evaluation of initial stage | | | evaluation of humid resistance | | |
|---|---|---|---|---|---|---|---|---|
| | | | B/M | toner | copied | Q/M | toner | copied |

TABLE 8-continued

| | Series | weight | agent No. | (μc/g) | flying | images/fogs | (μc/g) | flying | images/fogs |
|---|---|---|---|---|---|---|---|---|---|
| Example | A | 0.1 | XII-1 | +17 | ○ | ○ | +15 | ○ | ○ |
| | | 0.3 | VIII-3 | | | | | | |
| Example | B | 2 | XII-2 | +15 | ○ | ○ | +13 | ○ | ○ |
| | | 2 | VIII-2 | | | | | | |
| Example | C | 2 | XII-2 | +14 | ○ | ○ | +12 | ○ | ○ |
| | | 3 | I-10 | | | | | | |
| Example | D | 0.2 | XII-1 | +17 | ○ | ○ | +15 | ○ | ○ |
| | | 0.2 | II-3 | | | | | | |
| Example | E | 0.3 | XII-1 | +18 | ○ | ○ | +18 | ○ | ○ |
| | | 0.3 | II-19 | | | | | | |
| Example | H | 1 | XII-2 | +18 | ○ | ○ | +15 | ○ | ○ |
| | | 2 | I-31 | | | | | | |
| Example | I | 1 | XII-2 | +15 | ○ | ○ | +12 | ○ | ○ |
| | | 2 | X-4 | | | | | | |
| Example | J | 1 | XII-2 | +18 | ○ | ○ | +15 | ○ | ○ |
| | | 2 | X-14 | | | | | | |
| Example | J | 1 | VIII-3 | +17 | ○ | ○ | +14 | ○ | ○ |
| | | 1 | II-3 | | | | | | |
| Example | J | 0.5 | II-3 | +18 | ○ | ○ | +15 | ○ | ○ |
| | | 1.5 | X-13 | | | | | | |

| | Toner Series | parts by weight | charge controlling agent No. | evaluation of durability with respect to copy (copied images/fogs) | | | | | heat-resistance | translucence | fixing properties at high speed development | remarks |
|---|---|---|---|---|---|---|---|---|---|---|---|---|
| | | | | 1000 | 5000 | 10000 | 50000 | 100000 | | | | |
| | | | | | | (sheets) | | | | | | |
| Example | A | 0.1 | XII-1 | ○ | ○ | ○ | ○ | ○ | B | — | — | |
| | | 0.3 | VIII-3 | | | | | | | | | |
| Example | B | 2 | XII-2 | ○ | ○ | ○ | ○ | ○ | A | ○ | — | oil spread fixing |
| | | 2 | VIII-2 | | | | | | | | | |
| Example | C | 2 | XII-2 | ○ | ○ | ○ | ○ | ○ | A | — | — | |
| | | 3 | I-10 | | | | | | | | | |
| Example | D | 0.2 | XII-1 | ○ | ○ | ○ | ○ | ○ | A | ○ | — | oil spread fixing |
| | | 0.2 | II-3 | | | | | | | | | |
| Example | E | 0.3 | XII-1 | ○ | ○ | ○ | ○ | ○ | B | — | — | |
| | | 0.3 | II-19 | | | | | | | | | |
| Example | H | 1 | XII-2 | ○ | ○ | ○ | ○ | ○ | B | — | ○ | |
| | | 2 | I-31 | | | | | | | | | |
| Example | I | 1 | XII-2 | ○ | ○ | ○ | ○ | ○ | A | — | ○ | |
| | | 2 | X-4 | | | | | | | | | |
| Example | J | 1 | XII-2 | ○ | ○ | ○ | ○ | ○ | B | — | — | |
| | | 2 | X-14 | | | | | | | | | |
| Example | J | 1 | VIII-3 | ○ | ○ | ○ | ○ | ○ | B | — | — | |
| | | 1 | II-3 | | | | | | | | | |
| Example | J | 0.5 | II-3 | ○ | ○ | ○ | ○ | ○ | B | — | — | |
| | | 1.5 | X-13 | | | | | | | | | |

Hereinafter, examples are explained with respect to a toner constituted of suspension-polymerized polymer as a main resin.

SYNTHESIS EXAMPLES 1–4 OF SUSPENSION POLYMERIZED POLYMER

Twelve hundred grams of ion-exchanged water, 60 g of Supertite 10 (trade mark; water-dispersant of hydroxy apatite; 10% of solids; made by Nippon Kagaku Kogyo K.K.), 60 g of sodium chloride, specified grams of a mixture of monomers, polymerization initiator and, if desired, molecular weight modifier shown at the column of low molecular weight component in Table 9 were put into a separable flask with a capacity of 3 liters equipped with a stirrer, a condenser, a gas inlet tube and a thermometer. Nitrogen gas was introduced into the flask, and the contents were stirred at room temperature for 30 minutes to disperse them stably. The temperature was increased gradually up to for 1 hour at which temperature the contents were stirred for 3 hours. Then, the contents were maintained at 95° C. for 2 hours to complete the reaction. Thus, low molecular weight polymer was obtained. The weight average molecular weight, the number average molecular weight and the glass transition of the obtained low molecular weight polymer at this step were shown in Table 9.

Then, the contents in the flask were cooled to 50° C., thereafter, a mixture of monomers and polymerization initiator shown at the column of high molecular component in Table 9 were added into the flask and stirred at 50° C. for 2 hours. Sixty grams of Supertite 10 and 30 g of ion-exchanged water were further added to the contents, which were stirred at 50° C. for 1 hour for stable dispersion, heated gradually up to 85° C. for about 30 minutes, and stirred for 3 hours at that temperature. The contents were maintained at 90° C. for 1 hour, and at 95° C. for 2 hours, and then cooled to 40° C. to complete the reaction.

Concentrated hydrochloric acid of 30 ml was added to the resultant aqueous solution containing dispersed resin beads to adjust the pH to 2. Then the resin beads were filtrated in vacuum, washed with ion-exchanged water of 500 ml three times, and dried in a drier at 50° C. for 12 hours.

The obtained resin beads were sifted to comprise 1 percent by weight or less of particles finer than 50 meshes, 78 percents by weight or more of particles of 32–150 meshes and 1 percent by weight or less of particles rougher than 16 meshes, and further adjusted so that the ratio ($\overline{D}v/\overline{D}_1$) of average volume size ($\overline{D}v$) to number average size ($\overline{D}_1$) might be 1.04–1.40.

The average molecular weight, number average molecular weight, glass transition point and softening point of the obtained resin beads were shown in Table 9.

TABLE 9

|  | synthesis example | | | |
|---|---|---|---|---|
|  | 1 | 2 | 3 | 4 |
| low molecular weight components (ingredients (g)) | | | | |
| styrene | 640 | 640 | 640 | 480 |
| butyl acrylate | 160 | 160 | 160 |  |
| butyl methacrylate |  |  |  | 320 |
| benzoyl peroxide | 30 |  |  | 30 |
| lauryl peroxide |  |  | 40 |  |
| acetyl peroxide |  | 20 |  |  |
| dodecyl mercaptan | 4 |  |  |  |
| low molecular weight components (physical properties) | | | | |
| number average molecular weight *1 | 7,590 | 8,240 | 7,370 | 16,120 |
| weight average molecular weight *1 | 18,430 | 19,310 | 17,890 | 33,210 |
| glass transition point *2 | 75 | 72 | 65 | 70 |
| high molecular weight components (ingredients (g)) | | | | |
| styrene | 300 | 300 | 300 | 280 |
| butyl acrylate | 100 | 100 | 100 |  |
| butyl methacrylate |  |  |  | 120 |
| 3,3,5-trimethyl cyclohexanone ditertiarybutyl peroxyketal | 4 |  | 8 | 4 |
| cyclohexanone ditertiarybutyl peroxyketal |  | 0.5 |  |  |
| obtained resin beads (physical properties) | | | | |
| number average molecular weight *1 | 19,640 | 20,710 | 19,070 | 23,850 |
| weight average molecular weight *1 | 298,720 | 300,130 | 295,610 | 324,560 |
| glass transition point *2 | 65 | 65 | 53 | 62 |
| softening point *3 | 123 | 124 | 116 | 125 |

*1 [measuring conditions]
apparatus: Hitachi 635 type (made by Hitachi Seisakusho K.K.)
column: three columns with 10.7 (diameter) × 30 cm are directly connected. Each column are filled with Gel Pack R440, R450, R400M (made by Hitachi Kasei Kogyo K.K.) respectively.
column pressure: 35 kgf/cm$^2$
flow amount: 2.03 ml/min.
detector: detector of refractive index
*2 endo-and exothermic behavior observed by differential scanning thermal analysis the point where the maximum of the exotherm caused by glass transition is observed
*3 measured value by ring and ball method

SYNTHESIS EXAMPLE 5-8 OF SUSPENSION POLYMERIZED POLYMER

Twelve hundred grams of ion-exchanged water, the specified amount of Supertite 10 (trade mark; water-dispersant of hydroxy apatite; 10 % of solids; made by Nippon Kagaku Kogyo K.K.) shown at the column of first addition in Table 10 and 60 g of sodium chloride were put into a separable flask with a capacity of 3 liters equipped with a stirrer, a condenser, a gas inlet tube and a thermometer. Four hundred and eighty grams of styrene, 320 g of butyl methacrylate and 30 g of benzoylperoxide were put into another vessel and stirred sufficiently, and then the obtained solution was poured into the flask with a capacity of 3 liters above mentioned. Then, nitrogen gas was introduced into the flask, and the contents were stirred at room temperature for 30 minutes at revolution number as shown in Table 9 to disperse them stably. The temperature was increased gradually up to 90° C. for 1 hours, at which temperature the contents were stirred for 3 hours. Then, the contents were maintained at 95° C. for 2 hours to complete the reaction.

After the contents in the flask were cooled to 50° C., a mixture of 280 g of styrene, 120 g of butyl methacrylate and 6 g of 3,3,5-trimethyl-cyclohexanone ditertiarybutylperoxyketal was added thereto and stirred at 50° C. for 2 hours. Thereafter, 60 g of Supertite 10 for second addition and 30 g of ion-exchanged water were added into the flask to stir at 50° C. for 1 hour for stable dispersion. Then, the temperature was increased up to 85° C. for about 30 minutes, at which temperature the contents were reacted for 3 hours. Further, the contents were maintained at 90° C. for 1 hour, and at 95° C. for 2 hours, then cooled to 40° C. to complete the reaction.

Concentrated hydrochloric acid of 30 ml was added to the resultant aqueous solution containing dispersed resin beads to adjust the pH to 2 or less. Then the resin beads were filtrated in vacuum, washed with ion-exchanged water of 500 ml three times, and dried in a drier at 50° C. for 12 hours.

The obtained resin beads were sifted to comprise 1 percent by weight or less of particles finer than 50 meshes, 78 percents by weight or more of particles of 32 - 150 meshes and 1 percent by weight or less of particles rougher than 16 meshes, and further adjusted so that the ratio ($\overline{Dv}/\overline{D_1}$) of average volume size ($\overline{D}$) to number average size ($\overline{D_1}$) might be 1.04–1.40.

The average molecular weight, number average molecular weight, glass transition point and softening point of the obtained resin beads were shown in Table 10.

TABLE 10

| synthesis example | first addition Supertite 10 (g) | second addition Supertite 10 (g) | flask revolution number (rpm) | 150 meshes or rougher (wt/%) | 150~32 mesh (wt/%) | 16 meshes or finer (wt/%) | average volume size $\overline{Dv}$ |
|---|---|---|---|---|---|---|---|
| 5 | 60 | 60 | 320 | 0.7 | 93.2 | 0 | 0.38 |
| 6 | 60 | 60 | 280 | 0 | 84.5 | 0 | 0.41 |
| 7 | 45 | 60 | 320 | 0.6 | 78.6 | 0.4 | 0.48 |
| 8 | 30 | 60 | 300 | 0 | 46.4 | 17.5 | 0.94 |

| synthesis example | number average size $\overline{D_1}$ | $\overline{Dv}/\overline{D_1}$ | Tg *2 (°C.) | molecular weight *1 | | softening point *3 (°C.) | decrease *4 by heat (wt %) |
|---|---|---|---|---|---|---|---|
|  |  |  |  | MN ×10$^3$ | MW ×10$^3$ |  |  |
| 5 | 0.29 | 1.31 | 59 | 12 | 232 | 120 | 0.8 |
| 6 | 0.35 | 1.17 | 60 | 6 | 125 | 114 | 0.2 |
| 7 | 0.39 | 1.23 | 59 | 10 | 224 | 119 | 0.7 |

TABLE 10-continued

| | | | | | | | |
|---|---|---|---|---|---|---|---|
| 8 | 0.68 | 1.38 | 60 | 12 | 246 | 125 | 0.2 |

*1 [measuring conditions]
apparatus: Hitachi 635 type (made by Hitachi Seisakusho K.K.)
column: three columns with 10.7 (diameter) × 30 cm are directly connected. Each column are filled with Gel Pack R440, R450, R400M (made by Hitachi Kasei Kogyo K.K.) respectively.
column pressure: 35 kgf/cm$^2$
flow amount: 2.03 ml/min.
detector: detector of refractive index
*2 endo-and exothermic behavior observed by differential scanning thermal analysis the point where the maximum of the exotherm caused by glass transition is observed
*3 measured value by ring and ball method
*4 about one gram of particles of 0.3 mm or less (48 mesh) was weighed precisely and left in an oven at 110° C. for 2 hours. Thereafter, the decrease ratio was represented by percent by weight

EXAMPLE 13-20

| ingredients | parts by weight |
|---|---|
| (A) one of suspension polymerized resins obtained in the synthesis examples 1-8 | 100 |
| (B) styrene aminoacrylic resin as a charge controlling agents of [XII-3] | 2 |
| (C) one of imidazole compounds selected from [VIII-3], (VIII-4], [I-3], [II-3], [II-9], [II-19], [X-4] or [X-13] | 2 |
| (D) Copper-phthalocyanine pigments (#420; made by Dainichi Seika K.K.) | 5 |
| (E) low molecular weight polypropylene (Viscol 550P; made by Sanyo Kasei Kogyo K.K.) | |

The above ingredients were mixed sufficiently in a boll mill and kneaded in twin-screw extruding kneader to pulverize coarsely to the particles of about 5×5×5 mm or less). The obtained particles were pulverized finely by a jet grinder, followed by being air-classified to obtain particles of 13.5 μm in means particle size. The obtained fine particles were admixed with hydrophilic silica R-972 (made by Nippon Aerosil K.K.) cf 0.2 parts by weight to obtain a positively chargeable color toner. The amount of carboxylic acids and ketones which were decomposed residues of polymerization initiator in the toners were measured by gas chromatography. The results were shown in Table 12.

EXAMPLE 21

A toner was prepared in a manner similar to Example 20 except that one part by weight of imidazole compound I-3] and one part by weight of imidazole compound [X--13] were used.

EXAMPLE 22

A toner was prepared in a manner similar to Example 20 except that 0.5 parts by weight of imidazole compound [VIII-3] and 1.5 parts by weight of imidazole compound [I-3] were used.

COMPARATIVE EXAMPLES 6-8

Three kinds of toners were prepared in a manner similar to Example 13 except that three of suspension polymerized polymers prepared in the synthesis examples 1, 2 and 3 as a binder resin and quaternary ammonium salt (P-51; made by Orient Kagaku Kogyo K.K.) of 2 parts by weight as a charge controlling agent were used.

COMPARATIVE EXAMPLE 9

A toner was prepared in a manner similar to Example 13 except that the suspension polymerized polymer prepared in the synthesis example 1 and Nigrosine base EX (made by Orient Kagaku Kogyo K.K.) of 2 parts by weight as a charge controlling agents were used.

COMPARATIVE EXAMPLE 10

A toner was prepared in a manner similar to Example 13 except that the suspension polymerized polymer prepared in the synthesis example 1 and 2-aminobenzimidazole compound of 2 parts by weight as a charge controlling agent were used.

COMPARATIVE EXAMPLES 11 AND 12

Two kinds of toners were prepared in a manner similar to Example 13 except that two of suspension polymerized polymers prepared in the synthesis examples 5 and 8 as a binder resin and quaternary ammonium salt (P-51; made by Orient Kagaku Kogyo K.K.) of 2 parts by weight as a charge controlling agent were used.

Preparation of Microcarrier (2)

| ingredients | parts by weight |
|---|---|
| Pliolite ACL (styrene-acrylic copolymer; made by Good Year Chemical) | 100 |
| Mapico Black (magnetite; made by Tita Kogyo) | 200 |
| Carbon black Ma#8 (made by Mitsubishi Kasei Kogyo K.K.) | 4 |

The above mentioned ingredients were sufficiently mixed in a ball mill, thereafter being kneaded over a three-roller. The kneaded mixture was coarsely pulverized and finely pulverized in a jet mill, followed by being air-classified to obtain a micro-carrier of binder type of 35 μm in mean particle size.

Preparation of Microcarrier (3)

| ingredients | parts by weight |
|---|---|
| polyester of bisphenol type (tm: 122° C., Tg; 63° C.) | 100 |
| ferrite of Zn type (6S: 72 emu/g, Hc: 110) | 500 |
| carbon black MA#8 (made by Mitsubishi Kasei Kogyo K.K.) | 4 |

The above mentioned ingredients were sufficiently mixed in a Henschel mixer, thereafter being kneaded over a three-roller. The kneaded mixture was coarsely pulverized and finely pulverized in a jet mill, followed by being air-classified to obtain a microcarrier of binder type of 55 μm in mean particle size.

Evaluation of Toners (1) charge amount

A toner was mixed with the microcarrier (2) or (3) at 10 percents by weight to prepare a developer. Sixty grams of developer were put into a poly bottle of a capacity of 100 cc and stirred at 120 rpm for 3, 10 and 30 minutes to measure the charge amount (Qf).

(2) toner flying

A developer prepared by mixing a toner with a microcarrier for 3 minutes at the content of toner of 20 percents by weight was used.

The flying amount was measured with the use of a digital dust measuring apparatus (made by Shibata Kagakusha K.K.). Ten grams of the developer were set on the magnet roller with a sleeve mounted therearound, which was revolved at 1000 rpm Then, the dust measuring apparatus detected the toner particles flying about as a dust, and displayed the resultant value in the number of counts per minute, i.e. cpm.

When the cpm was 500 or less, such flying amount was normal and there was almost no troubles caused by toner flying in a practical copying machine. When the cpm was 500 or more, in particular, 1000 cpm or more, such a lot of toner flying resulted in dusts of copying machine and troubles such as fogs.

(3) decreasing ratio of charge ammount before and after left in high humid conditions A developer, once stirred for 30 minutes to measure charge amount Qf (30 minutes) was left to stand for 7 days with the cap of the bottle open under conditions of 35° C. and 85%, thereafter the charge amount (Qf(35° C., 85%, 7 days)) was measured to calculate a decreasing ratio of charge amount according to the formula below;

$$\text{Decreasing Ratio} = \frac{Qf(30 \text{ minutes}) - Qf(35° C., 85\%, 7 \text{ days})}{Qf(30 \text{ minutes})} \times 100$$

(4) Heat resistance test was carried out and evaluated as aforementioned.

(5) Fixing Properties

The generation of off-set at high temperature, the generation of off-set at low temperature and the fixing strength of I.D.1.2 and I.D.0.6 at 175° C. in fixing temperature were measured by fixing a toner through between a fixing roller (40 φ) coated with resin of teflon series and a LTV rubber roller which was compressed against the fixing roller at the pressure of 80 Kg, and passing there between at the revolution speed of 20 cm/sec.

(6) Durability test with respect to copy

A toner and microcarrier (2) were put into a polybottle with a capacity of 1 liter such that the toner was contained at 10 percents by weight. Then, the poly-bottle was revolved at 120 rmp for 10 hours to prepare a developer.

The obtained developer was subjected to durability test with respect to copy of 10000 sheets of copying paper with a copying machine EP450Z (made by Minolta Camera K.K.). The results were ranked as below;

5: no fogs
4: little fogs
3: a little fogs; no practical problems
2: much fogs
1: very much fogs The results of evaluations above mentioned were shown in Table 12.

TABLE 11

| toner | | example | | | | | | | |
|---|---|---|---|---|---|---|---|---|---|
| | | 1 | 2 | 3 | 4 | 5 | 6 | 7 | 8 |
| a mixture of vinyl polymer | | synthesis example | | | | | | | |
| | | 1 | 2 | 3 | 4 | 5 | 6 | 7 | 8 |
| decomposed *4 residue percent by weight | carboxylic acids | 0.3 | 0.05 | 1.7 | 0.3 | 0.4 | 0.3 | 0.3 | 0.4 |
| | ketones | 0.5 | 0.07 | 2.1 | 0.5 | 0.6 | 0.5 | 0.6 | 0.5 |

*4 measuring conditions
apparatus; Hitachi gas chromatograph 263 type
column and filter; material quality of column; made of glass; 1.5 × 3 mmφ
carrier; Chromosorb W 80/100
liquid phase; Thermon-1000 5% (made by Shinwa Kako K.K. + phosphoric acid 0.5%)
measuring temperature; 180° C.
carrier gas; N₂ 1.75 kgf/cm² detecter: FID
inner standard material; phthalic anhydride

TABLE 12

| | | charge amount | | | | | |
|---|---|---|---|---|---|---|---|
| | suspension | Carrier 1 | | | Carrier 2 | | |
| Toner | polymerized polymer | 3 min. (μc/g) | 10 min. (μc/g) | 30 min. (μc/g) | 3 min. (μc/g) | 10 min. (μc/g) | 30 min. (μc/g) |
| Example | Synthesis Example | | | | | | |
| 13 | 1 | 17 | 17 | 17 | 18 | 18 | 18 |
| 14 | 2 | 15 | 15 | 16 | 15 | 16 | 16 |
| 15 | 3 | 16 | 17 | 17 | 16 | 17 | 17 |
| 16 | 4 | 17 | 17 | 17 | 16 | 17 | 17 |
| 17 | 5 | 15 | 16 | 16 | 15 | 16 | 16 |
| 18 | 6 | 15 | 16 | 16 | 15 | 16 | 16 |
| 19 | 7 | 15 | 16 | 16 | 16 | 16 | 16 |
| 20 | 8 | 13 | 14 | 15 | 14 | 14 | 15 |
| 21 | 8 | 14 | 16 | 16 | 15 | 16 | 17 |
| 22 | 8 | 15 | 16 | 16 | 15 | 16 | 16 |
| Comparative Example | Synthesis Example | | | | | | |
| 6 | 1 | 14 | 16 | 16 | 15 | 16 | 17 |
| 7 | 2 | 8 | 10 | 12 | 9 | 12 | 13 |
| 8 | 3 | 12 | 14 | 16 | 13 | 14 | 16 |
| 9 | 1 | 9 | 12 | 15 | 8 | 13 | 16 |
| 10 | 1 | 10 | 13 | 15 | 9 | 12 | 15 |
| 11 | 5 | 13 | 15 | 16 | 14 | 15 | 16 |
| 12 | 8 | 8 | 10 | 13 | 8 | 11 | 14 |

| | | | heat | fixing properties | | | |
|---|---|---|---|---|---|---|---|
| | suspension polymerized | flying amount | charge amount | resistance | off-set/ width | I.D. | I.D. | durability test with respect to |

TABLE 12-continued

| Toner Example | polymer Synthesis Example | (cpm) | (%) | (rank) | (°C.) | 0.6 | 1.2 | copy (after 10K) |
|---|---|---|---|---|---|---|---|---|
| 13 | 1 | 54 | 6 | A | $\geq 122\sim 250°$ C. | 85 | 91 | 5 |
| 14 | 2 | 206 | 14 | A | $\geq 126\sim 250°$ C. | 78 | 93 | 4 |
| 15 | 3 | 147 | 12 | B | $118\sim 235°$ C. | 85 | 95 | 4 |
| 16 | 4 | 46 | 7 | A | $\geq 127\sim 250°$ C. | 83 | 94 | 5 |
| 17 | 5 | 245 | 8 | A | $\geq 123\sim 250°$ C. | 80 | 91 | 5 |
| 18 | 6 | 61 | 5 | A | $\geq 118\sim 250°$ C. | 88 | 98 | 5 |
| 19 | 7 | 87 | 10 | A | $\geq 124\sim 250°$ C. | 82 | 90 | 5 |
| 20 | 8 | 342 | 16 | A | $\geq 125\sim 250°$ C. | 78 | 88 | 4 |
| 21 | 8 | 214 | 12 | A | $\geq 125\sim 250°$ C. | 80 | 92 | 5 |
| 22 | 8 | 187 | 11 | A | $\geq 125\sim 250°$ C. | 81 | 95 | 5 |
| Comparative Example | Synthesis Example | | | | | | | |
| 6 | 1 | 78 | 21 | A | $\geq 121\sim 250°$ C. | 79 | 93 | 4 |
| 7 | 2 | 1976 | 37 | A | $\geq 122\sim 250°$ C. | 76 | 91 | 1 |
| 8 | 3 | 548 | 33 | E | $116\sim 205°$ C. | 84 | 98 | 2 |
| 9 | 1 | 212 | 28 | B | $\geq 120\sim 250°$ C. | 76 | 87 | 3 |
| 10 | 1 | 234 | 35 | B | $\geq 118\sim 250°$ C. | 74 | 86 | 3 |
| 11 | 5 | 324 | 21 | A | $\geq 122\sim 250°$ C. | 78 | 88 | 3 |
| 12 | 8 | 1688 | 48 | A | $\geq 124\sim 250°$ C. | 75 | 86 | 1 |

What is claimed is:

1. A toner for developing electrostatic latent images comprising at least a resin, a colorant, a wax of polyolefin series of low molecular weight which is added at a content of 1 to 10 parts by weight on the basis of 100 parts by weight of the resin, and particles of an imidazole compound functioning as a charge controlling agent and selected from the group consisting of an imidazole zinc complex represented by the general formula [I] below, an imidazole zinc compound represented by the general formula [II] below; and an imidazole derivative represented by the general formula [III] below;

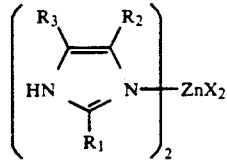
[I]

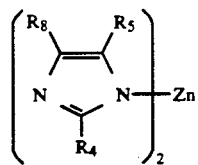
[II]

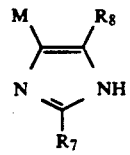
[III]

wherein $R_1$, $R_4$ and $R_7$ are respectively an alkyl group, an aralkyl group or an aryl group; $R_2$, $R_3$, $R_6$ and $R_8$ are respectively a hydrogen atom, an alkyl group, an aralkyl group or an aryl group; X represents a halogen atom, a hydroxy group or an ionic residual group of one valency; M represents a hydrogen atom, an alkyl group, an aralkyl group, an aryl group, a group represented by the general formula [V] below;

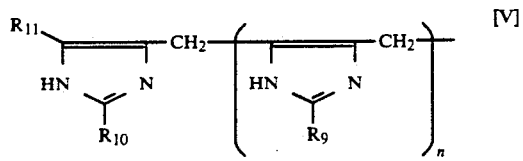
[V]

or a group represented by the general formula [VI];

[VI]

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1.

2. A toner of claim 1, wherein particles of the imidazole compound are dispersed in the resin.

3. A toner of claim 2, wherein the particles of the imidazole compound are dispersed at the content of 0.1-20 parts by weight on the basis of 100 parts by weight of the resin.

4. A toner of claim 2, wherein the particles of the imidazole compound are 5 μm or less in particle size.

5. A toner of claim 1, wherein the particles of the imidazole compound are fixed on the surface of the toner particles.

6. A toner of claim 5, wherein the particles of the imidazole compound are fixed by adhering them to the surface of toner particles with the help of van der Waals force and electrostatic force and then giving them mechanical impacts or the like.

7. A toner of claim 5, wherein the particles of the imidazole compound are added at the content of 0.001–10 parts by weight on the basis of 100 parts by weight of the toner.

8. A toner of claim 5, wherein the particles of the imidazole compound are 1 μm or less in particle size.

9. A toner of claim 1, which is positively chargeable.

10. A toner of claim 1, wherein the resin has the number average molecular weight (Mn) of 1000–7000, the ratio (Ms/Mn) of weight average molecular weight (Mw) to number average molecular weight (Mn) of 40–70, and the ratio (Mz/Mn) of Z average molecular weight (Mz) to number average molecular weight (Mn) of 200–500.

11. A toner of claim 1, which is a light-transmittable color toner.

12. A light-transmittable color toner for developing electrostatic latent images comprising at least
a linear polyester resin having 55° to 70° C. in glass transition point and 80° to 150° C. in softening point,
a colorant which is added at a content of 1 to 10 parts by weight on the basis of 100 parts by weight of the polyester resin, and
particles of an imidazole compound functioning as a charge controlling agent and selected from the group consisting of an imidazole zinc complex represented by the general formula [I] below, an imidazole zinc compound represented by the general formula [II] below and an imidazole derivative represented by the general formula [III] below;

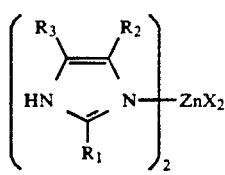
[I]

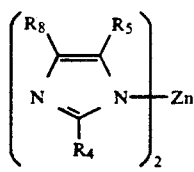
[II]

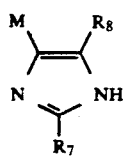
[III]

wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, an aralkyl group or an aryl group; X represents a halogen atom, a hydroxy group or an ionic residual group of one valency; M represents a hydrogen atom, an alkyl group, an aralkyl group, an aryl group, a group represented by the general formula [V] below;

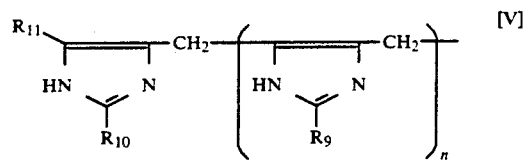
[V]

or a group represented by the general formula [VI];

[VI]

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer or more than 1.

13. A toner for developing electrostatic latent images comprising at least 'a resin,
a colorant, and
particles of an imidazole derivative functioning as a charge controlling agent and represented by the general formula [IX] below;

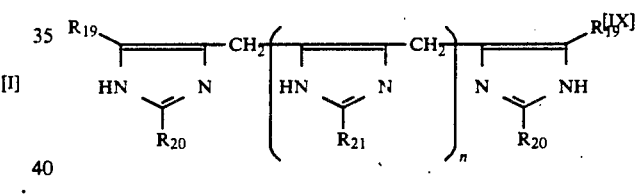
[IX]

wherein $R_{19}$, $R_{20}$ and $R_{21}$ are independently a hydrogen atom, an alkyl group, an aralkyl group or an aryl group; n is an integer of 1 or more.

14. A toner for developing electrostatic latent images comprising at least
a resin,
a colorant, and
particles of an imidazole derivative functioning as a charge controlling agent and represented by the general formula [XI] below;

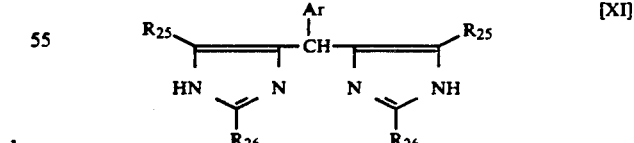
[XI]

wherein $R_{25}$ is an alkyl group; $R_{26}$ is an alkyl group, an aralkyl group, or an aryl group, each of which may have a substituent; Ar is an aryl group, or a residual group of heterocyclic ring, each of which may have a substituent.

15. A toner for developing electrostatic latent images comprising at least
a resin, a colorant, particles of an imidazole compound functioning as a charge controlling agent and selected from the group consisting of an imidazole zinc complex represented by the general formula [I] below, an imidazole zinc compound represented by the general formula [II] below and an imidazole derivative represented by the general formula [III] below; and a homopolymer of a nitrogen-containing vinyl monomer represented by the general formula [XII] below or a copolymer thereof with styrene;

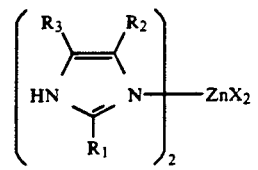  [I]

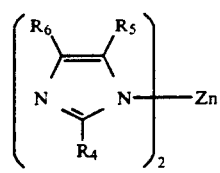  [II]

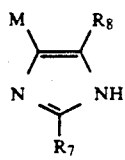  [III]

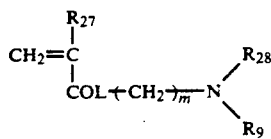  [XII]

wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, an aralkyl group or an aryl group; X represents a halogen atom, a hydroxy group or an ionic residual group of one valency; Y represents a hydrogen atom or a group represented by the formula [IV];

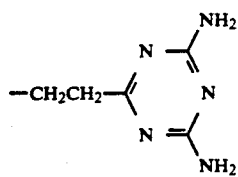  [IV]

M represents a hydrogen atom, an alkyl group, an aralkyl group, an aryl group, a group represented by the general formula [V] below;

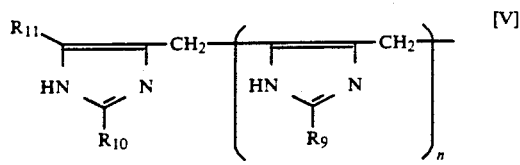  [V]

or a group represented by the general formula [VI];

  [VI]

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1, $R_{27}$ is a hydrogen atom or a methyl group; $R_{28}$ and $R_{29}$ are independently a $C_1$-$C_4$ alkyl group; L is an oxygen atom or an imino group; m is an integer of 1-4.

16. A toner of claim 15, wherein the particles of the imidazole compound selected from the general formulae [I]-[III] and the homopolymer of the nitrogen-containing vinyl monomer represented by the general formula [XII] or a copolymer thereof with styrene are dispersed in the resin.

17. A toner of claim 16, wherein the particles of the imidazole compounds selected from the general formulae [I]-[III] and the homopolymer of the nitrogen-containing vinyl monomer represented by the general formula [XII] or a copolymer thereof with styrene are dispersed totally at the content of 0.1-20 parts by weight on the basis of 100 parts by weight of the resin.

18. A toner of claim 15, wherein the particles of the imidazole compound selected from the general formulae [I]-[III] and the homopolymer of the nitrogen-containing vinyl monomer represented by the general formula [XII] or a copolymer thereof with styrene are fixed on the surface of the toner particles.

19. A toner of claim 18, wherein the particles of the imidazole compound selected from the general formulae [I]-[III] and the homopolymer of the nitrogen-containing vinyl monomer represented by the general formula [XII] or a copolymer thereof with styrene are added totally at the content of 0.001-10 parts by weight on the basis of 100 parts by weight of the toner.

20. A toner for developing electrostatic latent images comprising at least a suspension polymerized resin, a colorant, particles of an imidazole compound functioning as a charge controlling agent and selected from the group consisting of an imidazole zinc complex represented by the general formula [I] below, an imidazole zinc compound represented by the general formula [II] below and an imidazole derivative represented by the general formula [III] below; and a homopolymer of a nitrogen-containing vinyl monomer represented by the general formula [XII] below or a copolymer thereof with styrene;

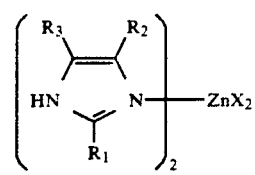 [I]

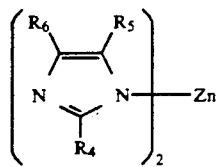 [II]

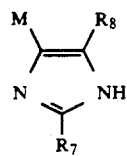 [III]

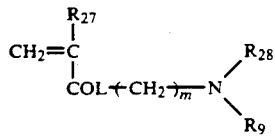 [XII]

wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, an aralkyl group or an aryl group; X represents a halogen atom, a hydroxy group or an ionic residual group of one valency; Y represents a hydrogen atom or a group represents by the formula [IV];

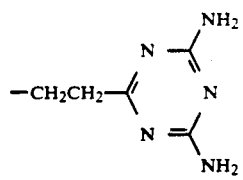 [IV]

M represented a hydrogen atom, an alkyl group, an aralkyl group, an aryl group, a group represented by the general formula [V] below;

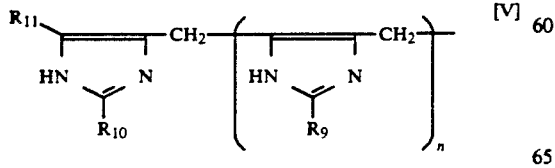 [V]

or a group represented by the general formula [VI];

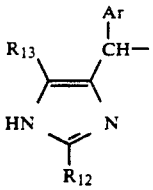 [VI]

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1, $R_{27}$ is hydrogen atom or a methyl group, $R_{28}$ and $R_{29}$ are independently a $C_1$-$C_4$ alkyl group; L is an oxygen atom or an imino group; m is an integer of 1–4.

21. A toner of claim 20, wherein the suspension polymerized resin comprises 1 percent by weight or less of particles finer than 150 meshes, .78 percent by weight or more of particles of 32–150 meshes, and 1 percent by weight or less of particles rougher than 16 meshes, and being adjusted to have the ratio of the average volume size (Dv) to the number average size (Dl) within the range of between 1.04 and 1.40.

22. A toner of claim 20, wherein the suspension polymerized resin comprises a low molecular weight vinyl polymer prepared with diacylperoxides as polymerization initiators and a high molecular weight vinyl-polymer prepared with peroxyketals as polymerization initiators.

23. A toner for developing electrostatic latent images comprising at least resin particles, and particles of an imidazole compound of 1 μm or less in particle size fixed to the surface of the resin particles by mechanical impact, said imidazole compound selected from the group consisting of an imidazole zinc complex represented by the general formula [I] below, an imidazole zinc compound represented by the general formula [II] below; and an imidazole derivative represented by the general formula [III] below;

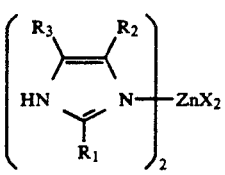 [I]

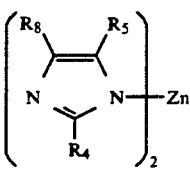 [II]

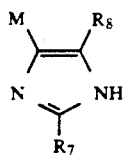

wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, an aralkyl group or an aryl group; X represents a halogen atom, a hydroxy group or an ionic residual group of one valency; Y represents a hydrogen atom or a group represented by the formula [IV];

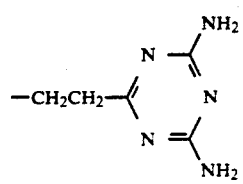

M represents a hydrogen atom, an alkyl group, an aralkyl group, an aryl group, a group represented by the general formula [V] below;

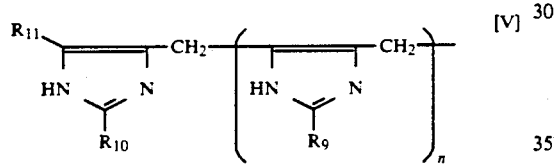

or a group represented by the general formula [VI];

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1.

24. A toner of claim 23, wherein said resin particles include a colorant.

25. A toner of claim 24, wherein the toner is obtained by the steps of mixing the resin particles with the particles of the imidazole compound, thereby to adhere the particles of the imidazole compound to the surface of the resin particles, and fixing the particles of the imidazole compound to the surface of the resin particles by mechanical impact.

26. A toner of claim 23, wherein the resin particles comprise core particles of a resin, a first layer of a colorant formed on the surface of the core particles and a second layer of fine particles of a resin formed on the surface of the first layer.

27. A toner of claim 26, wherein the toner is obtained by the steps of mixing the resin particles with the particles of the imidazole compound, thereby to adhere the particles of the imidazole compound to the surface of the resin particles, and fixing the particles of the imidazole compound to the surface of the resin particles by mechanical impact.

28. A toner for oilless fixing process comprising at least a resin having 55° to 80° C. in glass transition point and 80° to 150° C. in softening point, and contains gel components at a content of 5 to 20 percent by weight, a colorant, and particles of an imidazole compound functioning as a charge controlling agent and selected from the group consisting of an imidazole zinc complex represented by the general formula [I] below, an imidazole zinc compound represented by the general formula [II] below; and an imidazole derivative represented by the general formula [III] below;

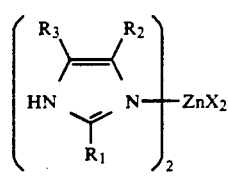

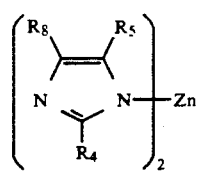

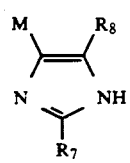

wherein $R_1$, $R_4$ and $R_7$ are respectively an alkyl group, an aralkyl group or an aryl group; $R_2$, $R_3$, $R_5$, $R_6$ and $R_8$ are respectively a hydrogen atom, an alkyl group, an aralkyl group or an aryl group; X represents a halogen atom, a hydroxy group or an ionic residual group of one valency; M represents a hydrogen atom, an alkyl group, an aralkyl group, an aryl group, a group represented by the general formula [V] below;

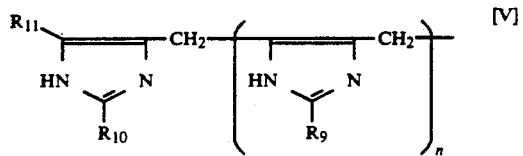

or a group represented by the general formula [VI];

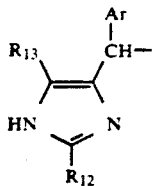 [VI]

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1.

* * * * *

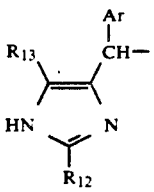 [VI]

wherein $R_9$, $R_{10}$ and $R_{12}$ are respectively an alkyl group, an aralkyl group or an aryl group; $R_{11}$ and $R_{13}$ are respectively a hydrogen atom, an alkyl group, an aralkyl group or an aryl group; Ar is an aryl group or a residual group of heterocyclic ring; n is zero or an integer of more than 1.

* * * * *

UNITED STATES PATENT AND TRADEMARK OFFICE
CERTIFICATE OF CORRECTION

PATENT NO. : 5,098,811
DATED     : March 24, 1992
INVENTOR(S) : Masahiro ANNO, et al.

It is certified that error appears in the above-identified patent and that said Letters Patent is hereby corrected as shown below:

On the title page, Item [54] and Col. 1, lines 1-3 should read:

TONER FOR DEVELOPING ELECTROSTATIC
    LATENT IMAGE COMPRISING SPECIFIED IMIDAZOLES

Signed and Sealed this

Twenty-ninth Day of June, 1993

Attest:

MICHAEL K. KIRK

Attesting Officer     Acting Commissioner of Patents and Trademarks